(12) United States Patent
Federspiel et al.

(10) Patent No.: US 7,763,097 B2
(45) Date of Patent: Jul. 27, 2010

(54) DEVICES, SYSTEMS AND METHODS FOR REDUCING THE CONCENTRATION OF A CHEMICAL ENTITY IN FLUIDS

(75) Inventors: William J. Federspiel, Pittsburgh, PA (US); Alan J. Russell, Gibsonia, PA (US); Heung-Il Oh, Pittsburgh, PA (US); Joel L. Kaar, Bryn Mawr, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 511 days.

(21) Appl. No.: 11/811,265

(22) Filed: Jun. 8, 2007

(65) Prior Publication Data

US 2008/0014622 A1    Jan. 17, 2008

Related U.S. Application Data

(60) Provisional application No. 60/811,810, filed on Jun. 8, 2006.

(51) Int. Cl.
B01D 53/22 (2006.01)

(52) U.S. Cl. .................. 95/46; 96/6; 96/8; 96/10; 96/11; 96/12; 95/45; 95/51; 95/54; 210/640; 210/500.21; 210/500.27; 210/506; 604/5.01; 604/6.14; 427/535; 427/569

(58) Field of Classification Search .................. 96/4, 96/6, 8, 10, 11, 12; 95/45, 46, 51, 54; 210/640, 210/641, 649, 500.21, 500.27, 506; 604/5.01, 604/6.14; 427/535, 569
See application file for complete search history.

(56) References Cited

U.S. PATENT DOCUMENTS 3,910,780 A * 10/1975 Henley et al. .............. 96/12
4,073,686 A    2/1978 Adams (Continued)

FOREIGN PATENT DOCUMENTS

GB    1 220 284    1/1971

(Continued)

OTHER PUBLICATIONS

Kaar, Joel L. et al.; Towards Improved Artificial Lungs Through Biocatalysis; Biomaterials; 28; (2007); pp. 3131-3139.

(Continued)

Primary Examiner—Jason M Greene
(74) Attorney, Agent, or Firm—Bartony & Associates LLC

(57) ABSTRACT

A device for removal of at least a portion of carbon dioxide from an aqueous fluid includes at least one membrane through which carbon dioxide can pass to be removed from the fluid and immobilized carbonic anhydrase on or in the vicinity of a first surface of the membrane to be contacted with the fluid such that the immobilized carbonic anhydrase comes into contact with the fluid. The first surface exhibits carbonic anhydrase activity of at least 20% of maximum theoretical activity of the first surface of the membrane based on monolayer surface coverage of carbonic anhydrase in the case that the carbonic anhydrase is immobilize on the first surface.

54 Claims, 11 Drawing Sheets

U.S. PATENT DOCUMENTS

| | | | |
|---|---|---|---|
| 4,112,052 | A | 9/1978 | Sartori |
| 4,602,987 | A | 7/1986 | Bonaventura |
| 4,761,209 | A * | 8/1988 | Bonaventura et al. .......... 95/54 |
| 5,132,108 | A | 7/1992 | Narayanan |
| 5,143,847 | A | 9/1992 | Kawase |
| 5,482,996 | A | 1/1996 | Russell |
| 5,614,378 | A * | 3/1997 | Yang et al. .................... 435/41 |
| 6,112,908 | A * | 9/2000 | Michaels .................... 210/506 |
| 6,143,556 | A | 11/2000 | Trachtenberg |
| 6,203,599 | B1 | 3/2001 | Schubert |
| 6,524,843 | B1 | 2/2003 | Blais |
| 6,946,288 | B2 | 9/2005 | Blais |
| 2001/0022952 | A1 | 9/2001 | Rau |
| 2003/0024881 | A1* | 2/2003 | Kalthod ...................... 210/649 |
| 2004/0029257 | A1 | 2/2004 | Dutil |
| 2004/0219090 | A1 | 11/2004 | Dziedzic |
| 2004/0259231 | A1* | 12/2004 | Bhattacharya .............. 435/266 |
| 2006/0014172 | A1* | 1/2006 | Muller et al. .................. 435/6 |
| 2006/0201874 | A1* | 9/2006 | Klare et al. ............ 210/500.36 |
| 2006/0263904 | A1* | 11/2006 | Morozov et al. ............ 436/518 |

FOREIGN PATENT DOCUMENTS

| | | |
|---|---|---|
| WO | WO 98/55210 | 12/1998 |
| WO | WO 2003/011359 | 2/2003 |
| WO | WO 2004/056455 | 7/2004 |
| WO | WO 2004/104160 | 12/2004 |
| WO | WO 2004/104160 A1 * | 12/2004 |
| WO | WO 2005/113817 | 12/2005 |
| WO | WO 2006/084276 | 8/2006 |
| WO | WO 2006/089423 | 8/2006 |
| WO | WO/2007/146162 | 12/2007 |

OTHER PUBLICATIONS

Broun, G. et al.; Facilitated Transport of CO2 Across a Membrane Bearing Carbonic Anhydrase; Febs Letters; vol. 7; No. 3; Apr. 1970; pp. 223-226.

Mancini II, Peter et al.; CO2 Removal for Ventilatory Support: A Comparison of Dialysis With and Without Carbonic Anhydrase to a Hollow Fiber Lung; ASAIO Journal; Trans 3; pp. 675-678.

Salley, S.O. et al.; Immobilized Carbonic Anhydrase in a Membrane Lung for Enhanced CO2 Removal; ASAIO Journal Trans 36;pp. 486-490 , 1990.

Sally, Steven O. et al.; Thermal, Operational, and Storage Stability of Immobilized Carbonic Anhydrase in Membrane Lungs; ASAIO Journal 1992;38(3); pp. 684-687.

Covalent Coupling Procedure on SiMAG-Hydroxyl by Cyanogen Bromide (CNBr) Activation; Chemicell GmbH; Coupling Protocol; SiMAG-Hxdroxyl 1.1; pp. 1-3.

Iwahashi Hidehiko et al. Development of the Oxygenator: Past, Present, and Future; J.Artif. Organs; 2004; 7; pp. 111-120.

Pocker, Y. et al.; The Catalytic Versatility of Erythrocyte Carbonic Anhydrase. IV. Kinetic Studies of the Esterase Activity and Competitive Inhibition by Substrate Analogs; Biochemistry; 1968; vol. 7; No. 9; pp. 3021-3031.

Pocker, Y. et al.; Carbonic Anhydrase: Structure, Catalytic Versatility, and Inhibition; Advances in Enzymology; Ed. Alton Meister; 47; 1978; pp. 149-274.

Kamo, J. et al. A New Multilayered Composite Hollow Fiber Membrane for Artificial Lung. Artificial Organs; 1990; Issue 5, (Abstract).

Federspiel, J. William, et al. 2004. Lung, Artificial: Basic Principles and Current Applications. Encyclo Biomat Biomed Eng; 2004; pp. 910-921.

Xu, Haiyan, et al.; Characterizing the Modification of Surface Proteins with Poly(Ethylene Glycol) to Interrupt Platelet Adhesion; Biomaterals; 2006;27; pp. 3125-3135.

Jensen, F.B.; Red Blood Cell pH, the Bohr Effect, and Other Oxygenation Linked Phenomena in Blood O2 and CO2 transport. Acta Physiol Scand; 2004; 182; pp. 215-227.

Cleland, Jeffrey L. et al.; Refolding and Aggregation of Bovine Carbonic Anhydrase B: Quasi-Elastic Light Scattering Analysis; Biochemistry; 1990; 29; pp. 11072-11078.

Stemler, Alan, An Assay for Carbonic Anhydrase Activity and Reactions that Produce Radiolabeled Gases or Small Uncharged Molecules; Anal Biochem; 1993; 210; pp. 328-331.

Lindskog, Sven et al.; The Catalytic Mechanism of Carbonic Anhydrase. Proc Natl Acad Sci USA; 1973; vol. 70; No. 9; pp. 2505-2508.

Smith, Ronald G.; Inorganic Carbon Transport in Biological Systems. Comp Biochem Physiol; 1988; vol. 90B, No. 4; pp. 639-654.

Axen, Rolf et al.; Chemical Fixation of Enzymes to Cyanogen Halide Activated Polysaccharide Carriers; Eur. J. Biochem; 1971; 18; pp. 351 360.

Hermanson, G. T.; The Chemistry of Reactive Groups; Bioconjugate techniques. San Diego, Academic Press; 1996; pp. 137-146.

Hermanson, G.T. et al.; Activation Methods; Immobilized affinity ligand techniques. San Diego, Academic Press; 2004; pp. 51-56.

Pariente, F. et al.; Enzyme Support Systems for Biosensor Applications Based on Gold-Coated Nylon Meshes; Biosens Bioelectronlcs; 1996;vol. 11; No. 11; pp. 1115-1128.

Drnovska, Hana, et al.; Surface Properties of Polyethylene After Low-Temperature Plasma Treatment; Colloid Polym Sci; 2003; 281; pp. 1025-1033.

Malpass, Charley A., et al.; Immobilization of an Oxalate-Degrading Enzyme on Silicone Elastomer;J Biomed Mater Res; 2002; 63; pp. 822-829.

Saito, Ryuta, et al.; Structure of Bovine Carbonic Anhydrase II at 1.95 A Resolution; Acta Cryst.; 2004; D60; pp. 792-795.

* cited by examiner

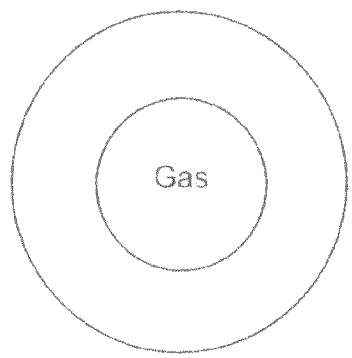
Fig. 13A
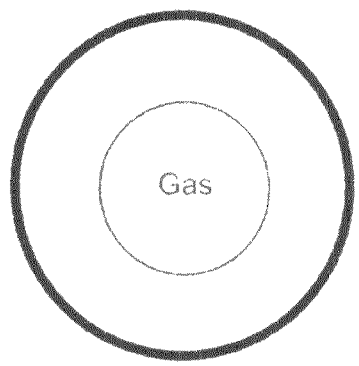
Fig. 13B
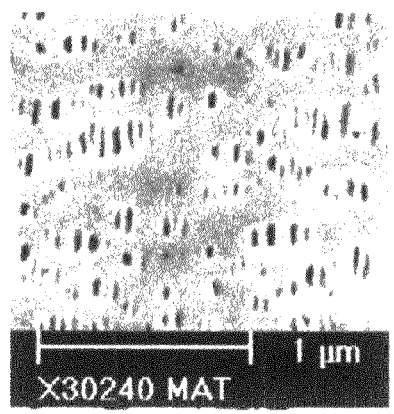
Fig. 13C
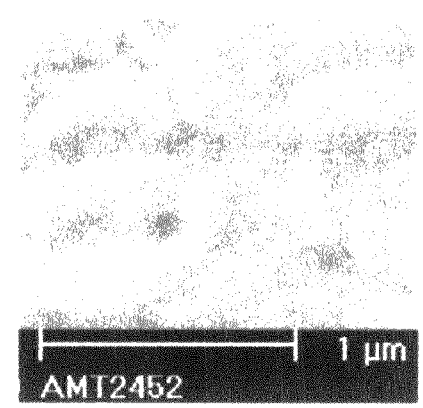
Fig. 13D
Fig. 14

DEVICES, SYSTEMS AND METHODS FOR REDUCING THE CONCENTRATION OF A CHEMICAL ENTITY IN FLUIDS

CROSS-REFERENCE TO RELATED APPLICATION

This application claims benefit of U.S. Provisional Patent Application Ser. No. 60/811,810, filed Jun. 8, 2006, the disclosure of which is incorporated herein by reference.

BACKGROUND OF THE INVENTION

The present invention relates generally to devices, systems and methods for reducing concentration of a chemical entity (for example, carbon dioxide) in fluids and, particularly, to devices, systems and methods for reducing concentration of a chemical entity (for example, carbon dioxide) in fluids such as blood in which an immobilized enzyme (for example, carbonic anhydrase) is used to facilitate diffusion toward a surface or membrane.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

Artificial lungs are employed to oxygenate the blood and to remove $CO_2$. Hollow fiber membrane (HFM) based artificial lungs began to replace bubble oxygenators in the 1980s. In that regard, HFM-based artificial lungs exhibit improved gas exchange performance as compared to bubble oxygenators. See Iwahashi H, Yuri K, Nose Y. 2004. Development of the oxygenator: past, present, and future. *J Artif Organs* 7:111-120. Nose developed the first HFM type artificial lung in 1971. However, the performance of early oxygenators was unacceptable as a result of fiber wetting and plasma leak problems. Nose Y, Malchesky P S. 1981; 3-14. Therapeutic membrane plasmapheresis. In: Therapeutic plasmapheresis. Oda T (ed) Stuttgart: F. K. Schattauer Subsequently, Kamo et al. developed commercially available composite fibers which were constructed with a true membrane layer between microporous walls. Kamo J, Uchida M, Hirai T, Yasuda H, Kanada K, Takemura T. 1990. A new multilayered composite hollow fiber membrane for artificial lung. Artificial Organs 14:369-372. Although, the composite fiber had excellent plasma wetting resistance, the permeance of the membrane was insufficient for intravenous oxygenation. Recent advances in membrane technology, however, have enabled the development of noble membranes such as polyolefin-based hollow fiber membrane that exhibit both good gas permeance and high plasma wetting resistance.

Currently available artificial lungs devices typically include bundles of microporous hollow fiber membranes through which oxygen passes while blood is perfused around the fibers. A review of artificial lungs and hollow fiber membrane technology is provided in Federspiel W J, Henchir K A. 2004. Lung, Artificial: Basic principles and current applications. *Encyclo Biomat Biomed Eng* 910-921, the disclosure of which is incorporated herein by reference. In general, oxygen is transferred from the lumen of the fibers into the blood; while $CO_2$ is transferred from the blood into the lumen of the fibers and is removed from the device. In the current artificial lung model, which is based on passive diffusion, the efficiency of $CO_2$ and $O_2$ gas exchange are limited by the fiber surface area to blood volume ratio. Gas exchange can be improved by increasing this ratio at the cost of increasing the overall size of the artificial lung device. Additionally, $CO_2$ removal rates are limited at lower blood flow rates.

Carbon dioxide is present in blood in three primary forms: $CO_2$ (dissolved), bicarbonate ($HCO_3^-$), or carbamate. As known in the chemical arts, $CO_2$ is interconvertible among these forms and the various forms can be in equilibrium with each other as described by a $CO_2$ dissociation curve. Most of the $CO_2$ in blood, however, exists in the form of $HCO_3^-$ in plasma and in red blood cells. Colton C K. 1976. Fundamentals of gas transport in blood. In: Zapol W M and Qvist J, editor. Artificial lungs for acute respiratory failure. Washington D.C.: Hemisphere Publishing Corporation. p 3-43. In that regard, approximately 94% of plasma $CO_2$ and 82% of red blood cell $CO_2$ is in the form of $HCO_3^-$. The two species are interconvertible via the reaction:

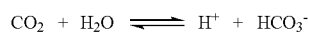

$$CO_2 + H_2O \rightleftharpoons H^+ + HCO_3^-$$

The $CO_2$ generates via metabolic pathways in tissue and diffuses into red blood cells (RBCs), where it is hydrated into $HCO_3^-$ and hydrogen ions ($H^+$) by intracellular carbonic anhydrase (CA). The hydrogen ions formed are bound to hemoglobin while $HCO_3^-$ is diffused into plasma. Jensen F B. 2004. Red blood cell pH, the Bohr effect, and other oxygenation linked phenomena in blood $O_2$ and $CO_2$ transport. Acta Physiol Scand 182:215-227. However, very little $CO_2$ is hydrated in plasma because of a lack of CA in plasma. In lungs, the reaction is reversed. $HCO_3^-$ is converted into $CO_2$ via CA in red blood cells, and then exhaled. Some CA exists in lung tissue.

CA (EC 4.2.1.1; MW 30,000 Da) is a metalloenzyme with a single zinc atom, which can effectively catalyze the reversible hydration and dehydration reaction of $CO_2$ ($CO_2 + H_2O \leftrightarrow H^+ + HCO_3^-$). Cleland J L, Wang D I C. 1990. Refolding and aggregation of bovine carbonic anhydrase B: Quasi-elastic light scattering analysis. Biochemistry 29:11072-11078; and Stemler. 1993. An assay for carbonic anhydrase activity and reactions that produce radiolabeled gases or small uncharged molecules. Anal Biochem 210:328-331. The enzyme enhances both hydration and dehydration rates over $10^5$-fold compared to reaction rates in the absence of CA, even though it is variable and depends on isoforms. Lindskog and Coleman, 1973 The catalytic mechanism of carbonic anhydrase. Proc Natl Acad Sci USA 70:2505-2508; Smith R G. 1988. Inorganic carbon transport in biological systems. Comp Biochem Physiol B 90:639-654. Once again, CA is usually found within RBCs and lung tissue (alveolar epithelium).

CA has been used for $CO_2$ processing in a number of devices. For example, U.S. Pat. No. 6,946,288 discloses the use of CA to reduce $CO_2$ levels in air. In addition, U.S. Pat. No. 6,524,843 discloses a CA immobilized bioreactor for the generation of $CO_2$. See also, U.S. Pat. No. 6,143,556 and Published PCT International Patent Application Nos. WO 2006/089413 and WO 2004-056455.

Moreover, a few studies have demonstrated that CA can improve $CO_2$ removal in an oxygenator. Salley et al. evaluated $CO_2$ removal efficiency using an encapsulated CA in cellulose nitrate. Salley S O, Song J Y, Whittlesey G C, Klein M D. 1990. Immobilized carbonic anhydrase in a membrane lung for enhanced $CO_2$ removal. ASAIO Trans 36:M486-490. Salley et al. immobilized CA containing microcapsules onto flat sheet type silicone rubber membrane. They obtained about 60% enhanced $CO_2$ removal rate (2.58 ml/min for untreated membrane and 4.15 mL/min for CA immobilized membrane). However, encapsulation resulted in an apparent 80% loss of CA activity, which likely negates the improvement in $CO_2$ exchange and enhanced storage stability of the encapsulated enzyme as was reported in Salley S O, Song J Y, Whittlesey G C, Klein M D. Thermal, operational, and storage stability of immobilized carbonic anhydrase in membrane lungs. ASAIO J 1 992; 38(3):M684-7. Mancini et al. performed $CO_2$ removal by employing extracorporeal $CO_2$ removal circuits which included a bubble oxygenator, a hollow fiber oxygenator to remove $CO_2$, and a dialyzer. Mancini II P, Whittlesey G C, Song J Y, Salley S O, Klein M D. 1990. $CO_2$ removal for ventilatory support: A comparison of dialysis with and without carbonic anhydrase to a hollow fiber lung. ASAIO Trans 36:M675-678. Mancini et al. compared $CO_2$ removal performance with and without free CA in the dialyzer. The $CO_2$ removal rates were found to be 8.76 mL/min without CA and 12.18 mL/min with CA. However, the studies failed to achieve $CO_2$ removal performance exceeding normal oxygenator using the relatively complex $CO_2$ removal system described therein.

Although previous studies have demonstrated the presence of CA can improve $CO_2$ gas exchange, the systems employed are not acceptable for practical use in, for example, artificial lung and other respiratory assist devices.

It remains desirable, for example, to develop improved artificial lung devices, systems and methods. Preferably, such devices, systems and methods are relatively simple in design and relatively efficient to manufacture and to operate.

SUMMARY OF THE INVENTION

In one aspect, the present invention provides a device for removal of at least a portion of carbon dioxide from an aqueous fluid, including: at least one membrane through which carbon dioxide can pass to be removed from the fluid and immobilized carbonic anhydrase on or in the vicinity of a first surface of the membrane to be contacted with the fluid such that the immobilized carbonic anhydrase comes into contact with the fluid. The first surface exhibits carbonic anhydrase activity of at least 20% of maximum theoretical activity of the first surface of the membrane based on monolayer surface coverage of carbonic anhydrase in the case that the carbonic anhydrase is immobilize on the first surface. In several embodiments, the first surface exhibits carbonic anhydrase activity of at least 40% of maximum theoretical activity of the fibers based on monolayer surface coverage of carbonic anhydrase. Further, the first surface can exhibit carbonic anhydrase activity of at least 60% of maximum theoretical activity of the first surface of the membranes based on monolayer surface coverage of carbonic anhydrase. Still further, the first surface can exhibit carbonic anhydrase activity of at least 80% of maximum theoretical activity of the first surface of the membrane based on monolayer surface coverage of carbonic anhydrase. Even higher activities are possible. Moreover, activities in excess of the maximum theoretical activity of the first surface of the membrane based on monolayer surface coverage of carbonic anhydrase in, for example, multilayered immobilization embodiments of the present invention. In multilayered embodiment, chemical chains including more than one carbonic anhydrase group are immobilized on the first surface. Carbon dioxide can, for example, be present in the fluid in the form of bicarbonate ion.

The fluid can, for example, be blood and the membrane can, for example, be formed from a polymeric material. The fluid can also, for example, be an oxygenated perfluorocarbon. The carbonic anhydrase can, for example, be immobilized on the polymeric material via adsorption, covalent bonding, ionic bonding or chelation. In several embodiments, the carbonic anhydrase is covalently attached to the polymeric material.

The polymeric material can, for example, be a microporous or permeable such that $CO_2$ can pass therethrough. In several embodiment, the polymeric material is microporous and sufficiently hydrophobic so that its pores remain gas filled after contacting blood or other aqueous fluids. The polymeric material can, for example, be an olefinic polymeric material.

In several embodiments, the carbonic anhydrase is covalently attached to the first surface of a microporous polymeric hollow fiber. The first surface can, for example, be an outer surface of the hollow fiber and an interior lumen of the hollow fiber can be adapted to have oxygen (or another carrier gas) flow therethrough. The hollow fiber can further be adapted to pass oxygen into the blood while carbon dioxide passes from the blood to the interior lumen of the hollow fiber. In several embodiments, the carbonic anhydrase is covalently attached to a permeable, nonporous polymeric coating on an exterior surface of a microporous polymeric hollow fiber. The device can include a plurality of membranes formed by a plurality of hollow fibers.

The at least one membrane can also include or be formed from a $CO_2$-permeable silicone.

The device can further include free carbonic anhydrase to contact the blood.

The device can, for example, be a component of a total liquid ventilation circuit adapted to be connected to lungs. The device can also use peritoneal or gastric perfusion to provide respiratory support. Further, the device can also, for example, be a component of an artificial lung.

The polymeric material can be treated prior to immobilizing the carbonic anhydrase thereon to create reactive sites on the polymeric material. The polymeric material can, for example, be treated via radio frequency plasma discharge to create reactive sites upon the polymeric material. The reactive sites can, for example, include at least one of a hydroxyl group, an amine group or a carboxyl group.

In another aspect, the present invention provides a method for removal of at least a portion of carbon dioxide from an aqueous fluid, including: placing at least one membrane through which carbon dioxide can pass to be removed from the fluid in contact with the fluid. The membrane includes immobilized carbonic anhydrase on or in the vicinity of a first surface thereof such that the immobilized carbonic anhydrase comes into contact with the fluid. The first surface exhibits carbonic anhydrase activity of at least 20% of maximum theoretical activity of the first surface of the membrane based on monolayer surface coverage of carbonic anhydrase in the case that the carbonic anhydrase is immobilized on the first surface of the membrane.

In several embodiments, the fluid is blood or, for example, an oxygenated perfluorocarbon. In several embodiments, the carbonic anhydrase is immobilized on the first surface of the membrane.

As described above, the first surface can exhibit carbonic anhydrase activity of at least 40% of maximum theoretical activity of the fibers based on monolayer surface coverage of carbonic anhydrase, of at least 60% of maximum theoretical activity of the fibers based on monolayer surface coverage of carbonic anhydrase, of at least 80% of maximum theoretical activity of the fibers based on monolayer surface coverage of carbonic anhydrase, or even higher.

The carbonic anhydrase can be immobilized, for example, on a polymeric material via adsorption, covalent bonding, ionic bonding or chelation. In several embodiments, the carbonic anhydrase is covalently bonded to the polymeric material. The carbonic anhydrase can, for example, be contacted with the polymeric material to react with reactive groups on the polymeric material. The reactive groups on the polymeric material can, for example, be reactive with amine groups on the carbonic anhydrase.

In several embodiments, the polymeric material is treated via radio frequency plasma discharge to create reactive sites upon the polymeric material. The reactive sites can, for example, include at least one of a hydroxyl group, an amine group or a carboxyl group.

In several embodiments, the polymeric material is contacted with a cyanogen halide to react hydroxyl groups thereon with the cyanogen halide. The carbonic anhydrase can be contacted with the polymeric material after contacting cyanogen halide with the polymeric material. The cyanogen halide can, for example, be cyanogen bromide.

Power levels during radio frequency plasma discharge and duration of radio frequency plasma discharge can be maintained to prevent substantially adverse effects upon the gas permeance of carbon dioxide through the polymeric material. Power levels during radio frequency plasma discharge and duration of radio frequency plasma discharge can also be maintained to prevent substantially adverse effects upon the gas permeance of oxygen through the polymeric material.

As described above, polymeric materials used in the present invention can, for example, be microporous or permeable. The polymeric material can, for example, be formed into a microporous hollow fiber having an interior lumen into which carbon dioxide can pass from the blood.

The method can further include causing oxygen to flow through the interior lumen of the microporous hollow fiber, whereby the oxygen can passes from the interior lumen into the blood.

In another aspect, the present invention provides a method of manufacturing a membrane for use in removal of carbon dioxide from an aqueous fluid including: immobilizing carbonic anhydrase on a first surface of a polymeric material via adsorption, covalent bonding, ionic bonding or chelation such that the first surface exhibits carbonic anhydrase activity of at least 20% of maximum theoretical activity of the first surface based on monolayer surface coverage of carbonic anhydrase.

In several embodiments, the carbonic anhydrase is covalently attached to the first surface of the polymeric material, and the first surface of the polymeric material is treated prior to immobilizing the carbonic anhydrase thereon to create reactive sites on the polymeric material. As described above, the first surface of the polymeric material can be treated via radio frequency plasma discharge to create reactive sites upon the first surface of the polymeric material. The created reactive sites can, for example, include at least one of a hydroxyl group, an amine group or a carboxyl group.

In another aspect, the present invention provides a device for removal of at least a portion of carbon dioxide from an aqueous fluid, including: at least one membrane through which carbon dioxide can pass to be removed from the fluid and immobilized carbonic anhydrase in the vicinity of a first surface of the membrane in contact with the fluid such that the immobilized carbonic anhydrase comes into contact with the fluid. The carbonic anhydrase can, for example, be immobilized on a material positioned in the vicinity of the at least one or surface. The material can, for example, be a metal. In several embodiments, the material is gold. The gold can, for example, be in the form of nanoparticles.

In still another aspect, the present invention provides a device for removal of at least a portion of chemical entity from a fluid, including: at least one membrane through which the chemical entity can pass as a gas to be removed from the fluid and immobilized enzyme on or in the vicinity of a first surface of the membrane to be contacted with the fluid such that the immobilized enzyme comes into contact with the fluid. The first surface can exhibit enzyme activity of at least 20% of maximum theoretical activity of the first surface based on monolayer surface coverage of enzyme in the case that the enzyme is immobilize on the first surface. The chemical entity is inter-convertible within the fluid to at least one other chemical entity. The enzyme is functional to catalyze a reaction of the other chemical entity to the chemical entity (to be removed).

In several embodiments, the devices, systems and methods of the present invention can easily be incorporated or retro-fitted into existing artificial lung devices and/or respiratory assist devices. In the case of artificial lung devices and/or respiratory assist devices including a membrane or membranes such as hollow fiber membranes, for example, no additional components are required as compared to existing devices. The manufacture requires only the additional process of immobilizing CA (for example, via covalent bonding) on, for example, the outer surfaces of membranes and/or hollow fibers. The operation of the artificial lung devices remains the same, while $CO_2$ removal is significantly improved. The significant improvement in the rate of $CO_2$ removal provided by the devices of the present invention can result in corresponding decreases in the total membrane surface area and a reduction in overall device size required in systems for removal of $CO_2$. This can, for example, be a significant advantage in the development of implantable artificial lungs.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 13A illustrates a cross-sectional representation of a microporous hollow fiber without a nonporous, permeable coating.

FIG. 13B illustrates a cross-sectional representation of a microporous hollow fiber with a nonporous, permeable coating.

FIG. 13C illustrates a scanning electron micrograph of a microporous hollow fiber without a nonporous, permeable coating.

FIG. 13D illustrates a scanning electron micrograph of a microporous hollow fiber with a nonporous, permeable coating.

FIG. 14 illustrates a scanning electron micrograph of an HFM fabric in which woven support threads are used to connect the hollow fibers.

DETAILED DESCRIPTION OF THE INVENTION

Figure 1A:
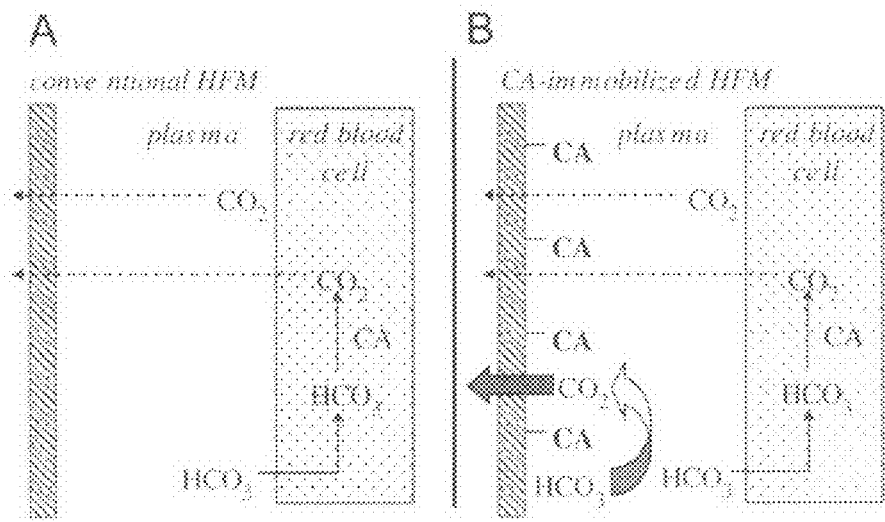
FIG. 1A illustrates a comparison of the operation of a standard hollow fiber membrane with a membrane of the present invention in which diffusion is faciliated by carbonic anhydrase immobilized on or in the vicinity of the membrane surface in contact with the bloodplasma. The facilitation occurs because the immobilized enzyme generates diffusion of bicarbonate ion (an alternative form of $CO_2$), which is a substrate of the enzyme, towards the membrane. At the membrane the bicarbonate ion is converted to $CO_2$ which then diffuses into and across the membrane.

As used herein and in the appended claims, the singular forms "a," "an", and "the" include plural references unless the content clearly dictates otherwise. Thus, for example, (unless clearly indicated otherwise) reference to "a chemical entity", to "a membrane" or to "a hollow fiber" includes a plurality of such chemical entities, membranes or hollow fibers and equivalents thereof known to those skilled in the art, and so forth, and reference to "the chemical entity", to "the membrane" or to "the hollow fiber" is a reference to one or more such chemical entities, membranes or hollow fibers and equivalents thereof known to those skilled in the art, and so forth.

As set forth above, the present invention provides devices, systems and methods for reducing the concentration of a chemical entity in fluids (for example, liquids, gases and combinations thereof). In several representative embodiments set forth below, the present invention is illustrated by setting forth devices, systems and methods for reducing the concentration of carbon dioxide in fluids such as blood in which immobilized carbonic anhydrase is used to facilitate diffusion toward a membrane including the immobilized enzyme. One skilled in the art, appreciates that the concepts of the present invention are applicable to enzymes generally as used in devices, systems and method to remove at least a portion of a chemical entity from a fluid. Moreover, the methods of immobilizing enzymes set forth in the present invention are applicable generally to any enzyme.

It was hypothesized that the rate of $CO_2$ removal could be considerably accelerated through adding free CA and/or immobilizing CA in the vicinity of or upon at least the outer surface of a gas permeable polymeric material such as the HFMs of an artificial lung and other devices. In that regard, and without limitation to any mechanism, it was hypothesized that the enzyme would catalyze the conversion of bicarbonate in the blood to $CO_2$, which can diffuse into the lumen of the fibers and be excreted, thereby facilitating active gas exchange. Increasing the efficiency of $CO_2$ removal is important in the use of HFMs in respiratory assist devices because the natural concentration gradient for $CO_2$ diffusion is much smaller than that for $O_2$ addition, resulting in a blood flow-dependent limitation to exchange. Furthermore, in many patients with respiratory failure the need for $CO_2$ removal is more important clinically, as oxygenation can be provided by nasal cannula or by low tidal volume, lung-protective ventilation Human tissues face the same diffusional challenges, and blood cells and the surface of the lung are coated with carbonic anhydrase, which accelerates diffusion across the small gradient. As discussed above, CA is present in red blood cells and on the endothelial surfaces of lung capillaries to aid in the carriage and exchange of $CO_2$. By catalyzing the reversible hydration of $CO_2$ into carbonic acid, which then rapidly dissociates into bicarbonate ion, CA substantially increases the $CO_2$ carrying capacity of blood, with over 90% of the $CO_2$ carried in blood being in the form of bicarbonate.

In several embodiments of the present invention, "bioactive" membrane systems such as bioactive HFM systems were developed to, for example, improve respiratory assist devices for $CO_2$ removal in lung failure patients. Employing a biomimetic approach, CA was immobilized on or in the vicinity of the surface of, for example, conventional HFMs, enabling "facilitated diffusion" of $CO_2$ as bicarbonate towards the HFM and enhancing the removal rate of $CO_2$. FIG. 1A illustrates a comparison of the operation of a standard hollow fiber membrane with a membrane of the present invention in which diffusion is facilitated by CA immobilized on (or in the vicinity of) the membrane surface in contact with the plasma.

With reference to FIG. 1A, in the present invention, removal of a specific chemical entity (for example, $CO_2$) from a fluid (for example, blood) is facilitated via enzyme-catalyzed reaction. The chemical entity to be removed exists within the fluid in one or more different chemical forms or as one or more other chemical entities (for example, the chemical entity $CO_2$ can exist as $HCO_3$, $H_2CO_3$ etc). The different forms of the chemical entities should be inter-convertible within the fluid and may or may not be in equilibrium with each other. At least one of the other forms of the specific chemical entity to be removed is a substrate for an enzyme that can convert the other form(s) to the specific chemical entity to be removed. In general, the chemical entity to be removed will have a non-negligible partial pressure and can exist as a gas under the operating conditions to pass through a gas porous or gas permeable membrane. The other form(s) of the chemical entity are typically solutes that cannot exist as a gas under the operating conditions and cannot pass through the membrane. The immobilized enzyme facilitates diffusion of the specific chemical entity through the membrane by generating diffusion of least one of the other forms of the entity to the surface of the membrane. At the membrane surface the enzyme converts at least one of those other forms to the specific form (the chemical entity) to be removed.

The studies of the present invention illustrated that CA maintains substantial activity upon immobilization (for example, via covalent bonding to a polymeric material). Immobilization may, for example, provide increased activity as compared to encapsulation (in which access to the CA can be hindered). Immobilization can, for example, be effected via adsorption, chemical bonding or chelation. Preferably, relatively strong attachments are used in immobilization such as covalent bonding, ionic bonding or chelation.

In several representative studies of the present invention, combined radio frequency glow discharge (RFGD) and cyanogen bromide (CNBr) activation chemistry was used to immobilize CA on an outer surface of the HFM via covalent bonding under experimentally determined conditions. In that regard, conditions were developed that, for example, did not substantially negatively affect the structural integrity of the HFM. To characterize the surface of the HFM before and after the CA modification, SEM analysis and gas permeance measurements were employed. The impact of enzyme activity levels of free and immobilized CA on $CO_2$ removal were also studied using an HFM mini-lung module. $CO_2$ removal studies were performed using bicarbonate solution using both free and immobilized CA in the mini-lung module as a small scale artificial lung. Once again, bicarbonate in the plasma is the primary form of $CO_2$ found in blood.

Figure 1B:
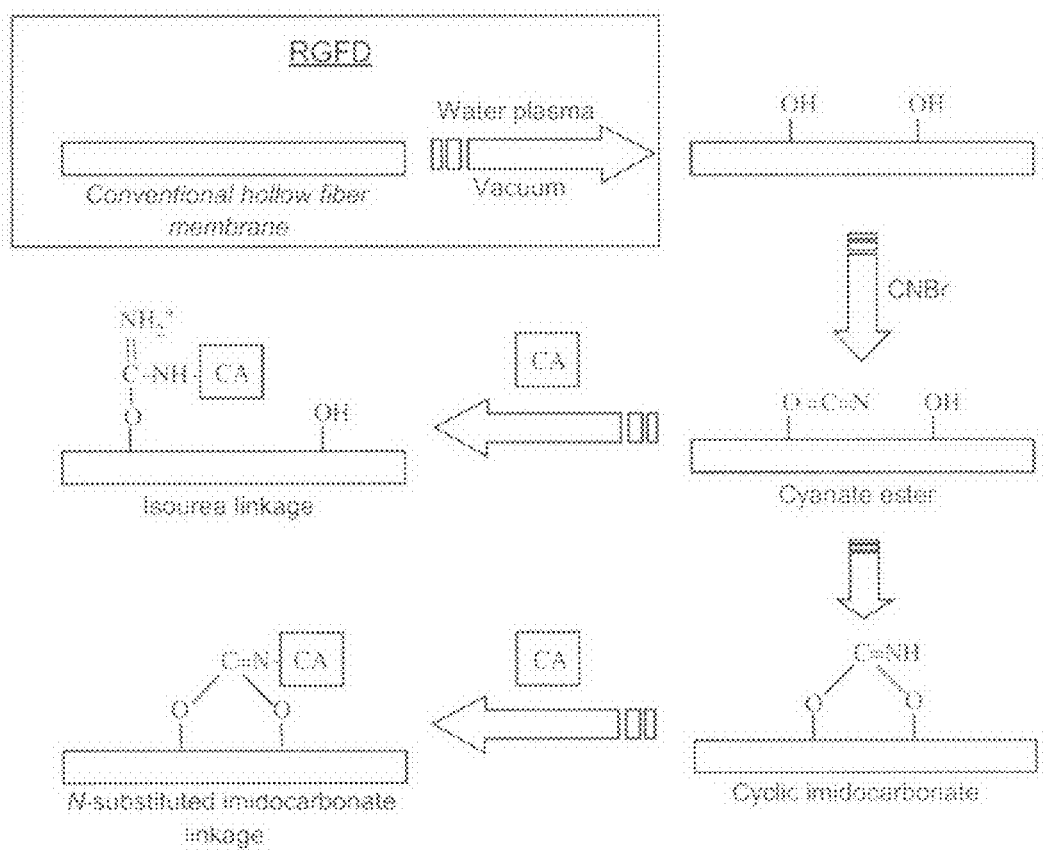
FIG. 1B illustrates an RFGD apparatus, a mechanism for immobilization of carbonic anhydride on a polymeric material.

As illustrated, for example, in FIG. 1B, CA was immobilized onto the fiber surface via initially introducing hydroxyl groups onto the fibers using radio frequency glow discharge (RFGD). The hydroxyl groups were subsequently converted to an imidocarbonate intermediate by the addition of cyanogen bromide. CNBr and other cyanogen halide immobilization chemistry is reviewed, for example, in Axén, R. and Ernback, S, (1971), Chemical Fixation of Enzymes to Cyanogen Halide Activated Polysaccharide Carriers, *Eur. J Biochem*, 18:351-360. Incubation with a solution of CA enabled the reaction between the cyanogen bromide-activated fibers and surface hydroxyls to convert the surface hydroxyls to cyanate esters and cyclic imidocarbonate to which CA can subsequently be reacted with forming covalent isourea and N-substituted imidocarbonate linkage. Parameters that impact the enzyme coupling reaction include the concentration of CA relative to the number of activated fibers, pH of the reaction buffer, and reaction time, The immobilization of CA (and/or other enzymes) to the HFMs and/or other polymeric materials is not limited to the above-described chemistry. Alternative routes of immobilization include introducing amine groups onto the fiber surface via RFGD and subsequently conjugating CA to the amines using glutaraldehyde as a crosslinker. CA may also be immobilized via the use of photocrosslinkers such as N-succinimidyl 4-benzoylbenzoic acid through a two step conjugation process. In the first step, the HFMs are activated by modification with one end of the crosslinker. Benzoylbenzoic acid, for example, can be reacted to the poly(methyl pentene) backbone by irradiation with UV (350-380 nm) light. Upon activation of the fibers, CA can then be conjugated to the other end of the crosslinker, which should contain a protein reactive functional group. The N-succinimidyl group is commonly employed on protein reactive crosslinkers because it reacts rapidly with amines in the protein under ambient temperature and physiological pH. Other routes for covalently immobilizing CA onto a polymer (for example, a hollow fiber membrane) surface include biotinylation of CA and subsequent binding to streptavidin-modified polymer and incorporation of CA into a polymer coating that can be wrapped around the fiber bundles without affecting gas exchange. In the synthesis of CA-immobilized coatings, functional groups on the enzyme's surface enable multipoint covalent incorporation of the enzyme directly into the polymer matrix, thus preventing leaching of the enzyme. As described above, CA may also be attached to the HFMs, although non-covalently, through, for example, physical adsorption, ionic interaction or chelation.

Chemical attachment techniques relevant to attachment of enzymes to, for example, polymeric materials are discussed generally, for example, in Hermanson, G. T. (1996). *Bioconjugate techniques*. San Diego, Academic Press and Hermanson, G. T., A. K. Mallia, et al. (1992). *Immobilized affinity ligand techniques*. San Diego, Academic Press.

Additionally, CA and/or other enzymes can be incorporated into the polymeric matrix or backbone of a polymer. For example, active CA and/or other enzymes can be incorporated into polyurethanes as described, for example, in U.S. Pat. No. 5,482,996.

Non-polymeric materials such as metals may also be employed as suitable support structures/surfaces for enzyme immobilization (such as in CA-immobilization in, for example, an artificial lung application). Amines and thiols, which are present on the surface of enzymes, react rapidly with a variety of metals including gold and silver and thus, in many cases, eliminate the need to pre-activate the metallic substrate. Bifunctional crosslinking agents which form self-assembling monolayers on metal surfaces are also used to covalently attach enzymes such as in the construction of amperometric biosensors (Pariente F, La Rosa C, Galan F, Hernándndez L, Lorenzo E. Enzyme support systems for biosensor applications based on gold-coated nylon meshes. *Biosens Bioelectron* 1996; 11:1115-1125.). CA can potentially be immobilized to nano or micro sized metallic particles whose primary role in, for example, an artificial lung is to disrupt diffusional boundary layers on the HFMs.

In the representative studies of the present invention, RFGD treatment was used as the first and primary step in introducing functional groups on the fibers to enable surface attachment of CA. However, several reports have shown RFGD to alter surface properties such as surface roughness and to cause surface damage. See, for example, Drnovská H, Lapcik Jr L, Buršikova V, Zemek J, Barros-Timmons A M. 2003. Surface properties of polyethylene after low-temperature plasma treatment. Colloid Polym Sci 281:1025-1033 and Malpass C A, Millsap K W, Sidhu H, Gower L B. 2002. Immobilization of an oxalate-degrading enzyme on silicone elastomer. J Biomed Mater Res 63:822-829. Preferably, the RFGD modification for surface activation of the HFM does not substantially affect or alter the original gas permeance characteristics, which could, for example, indicate surface defects that would allow blood plasma into membrane pores and cause decreases in gas permeance. Consequently, the physical integrity of the HFMs after RFGD plasma treatment was investigated by measuring gas permeance and by scanning electron microscope (SEM) analysis.

Gas permeance (Km) is a measure of the speed with which a gas can diffuse across a membrane. The gas permeance is the amount of gas flow per unit area of membrane that would arise from a unit difference in gas partial pressure across the membrane. For $CO_2$, the gas permeance is given by $$K_m = \frac{\dot{V}_{CO2}}{A \Delta P_{CO2}}$$

where $\dot{V}_{CO2}$ is the $CO_2$ flowrate across the membrane, A is the membrane area, and $\Delta P_{CO2}$ is the partial pressure difference of $CO_2$ across the membrane.

For artificial lung applications it is important that Km be large enough that $CO_2$ removal is not limited by diffusion across the membrane. For this reason microporous fibers were developed to replace the nonporous silicone membranes used in earlier artificial lung and blood oxygenator designs. Microporous fibers are fabricated using a variety of techniques to create submicron sized voids or pores in the polymer during membrane fabrication. For example, the membrane may be stretched during extrusion of the polymer as it leaves the dye or spinneret. The stretching causes defects (openings, pores, voids etc) to form in the polymer melt as it is crystallizing. These pores remain permanent once the fiber is cooled and conditioned at normal temperatures. Typically the porosity of these membranes range from 30-50%.

A microporous hydrophobic membrane has a much greater Km than a nonporous polymer membrane. If the pores remain gas filled, a microporous membrane allows gas diffusion through a gas phase rather than a solid polymer phase, as would occur in nonporous polymer membranes. The diffusion coefficients in gases are substantially higher than those in solid nonporous polymers. For this reason, the Km for a microporous membrane with a thickness of 25 microns (a typical membrane wall thickness in hollow fibers) varies from about 10 ml $CO_2$ $cm^2$/s/cmHg to $10^{-1}$ ml $CO_2/cm^2$/s/cmHg. In contrast, a nonporous silicone-type membrane (siloxane polymers are some of the most gas permeable) of the same thickness would have a Km of about $10^{-6}$ ml $CO_2/cm^2$/s/cmHg to $10^{-5}$ ml $CO_2/cm^2$/s/cmHg. A permeance this small limits the $CO_2$ removal rate of the membrane and the device in which the membrane is incorporated.

In artificial lung and blood oxygenator applications microporous membranes can "wet-out". Plasma seeps into the pores and dramatically decreases the Km of the membrane. For this reason, microporous membranes have been developed that have thin regions or layers of nonporous polymer on the blood-contacting side of the membrane. The membranes are either of asymmetric or composite design as discussed further below. These nonporous polymer layers block plasma infiltration but also reduce the permeance of the membrane. It is important that the nonporous polymer regions be thin compared to the thickness of the membrane. Typically, if siloxane nonporous polymers are coated on microporous membranes the coating is less than approximately 1 micron.

Preferably, the membrane Km for $CO_2$ in artificial lungs and blood oxygenators should be greater than $10^{-2}$ ml $CO_2/cm^2$/s/cmHg. Such membranes will have a negligible effect on $CO_2$ removal from the device. A permeance this high is difficult to achieve if an asymmetric or composite membrane is needed to prevent plasma wetting by blood. Practically then, a permeance greater than $10^{-3}$ ml $CO_2/cm^2$/s/cmHg is desired and achievable for asymmetric and composite fibers. Such membranes would affect $CO_2$ removal by less than 5-10% under nominal operating conditions.

Figure 2A:
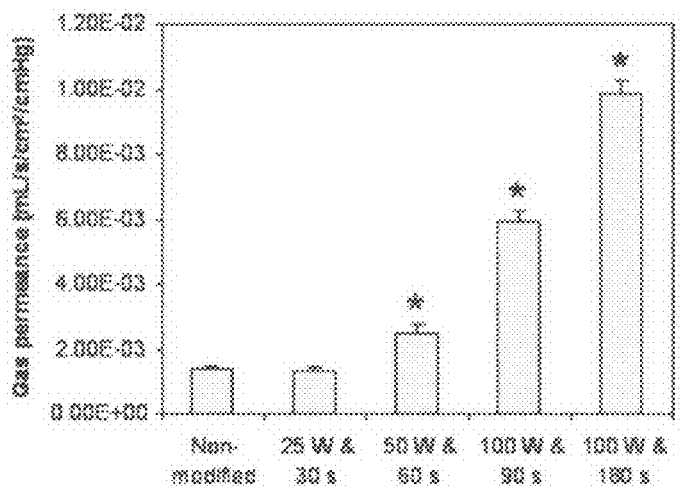
FIG. 2A illustrates a study of the effect of RFGD treatment power and treatment duration on gas permeance of polymethyl-pentene (PMP) hollow fiber membranes wherein $CO_2$ was used as a gas source and the designation * represent that p<0.05 between the sample and the control (unmodified fiber).

To study the effect of RFGD plasma treatment on gas permeance, a range of RFGD modification conditions for coupling of CA onto the outer surface of HFMs of the artificial lungs was studied. As illustrated in FIG. 2A, the gas permeance of the HFM was found to increase significantly with increasing exposure time and discharge power of the RFGD treatment. The gas permeance is a measure of the integrity of the surface of the PMP fiber, which was an asymmetric fiber in which the porosity goes to zero at the fiber surface. If permeance increases significantly this indicates that the fiber surface has been compromised by the RFGD treatment and would likely increase the potential for blood plasma wetting.

Samples treated at 50 W for 60 s, 100 W for 90 s, and 100 W for 180 s exhibited increased gas permeances of about 1.85-, 4.30-, and 7.61-fold (using $CO_2$ as a gas source), respectively, compared to unmodified membrane (control).

These RFGD treatment conditions induced statistically significant differences in gas permeance compared to the control (p<0.02 between the sample and the control). In contrast, no change of gas permeance was observed in the sample treated at 25 W power for 30 s in comparison with the unmodified fiber regardless of gas source (p>0.06). For HFM exhibiting desirable gas permeances, increases in gas permeance are preferably minimized. In general, it is preferred that gas permeances increase by less then 25%, and, more preferably, by less than 10%. Even more preferably, gas permeance changes by less than 5%. In general, power can be preferably maintained at 50 W or less in the RGFD used in the studies of the present invention. As power is increased, however, duration of treatment should be decreased. For example, at 50 W, a treatment time of 30 s can result in an increase in gas permeance of about 50%.

These results indicated RFGD treatment damaged the structural integrity of the fibers when sufficient power was used for a sufficient period of time. However, among the RFGD treatment conditions tested, the 25 W and 30 s treatment did not cause physical damage on the outer surface of the fibers as indicated by gas permeance testing of FIG. 2A and SEM analysis set forth in FIG. 2B (which is discussed further below). As also discussed further below, the 25 W and 30 s RFGD treatment conditions provided for a relatively good enzyme immobilization efficiency of approximately 80% surface coverage using 1 mg/mL of CA in a coupling solution.

Figure 2B:
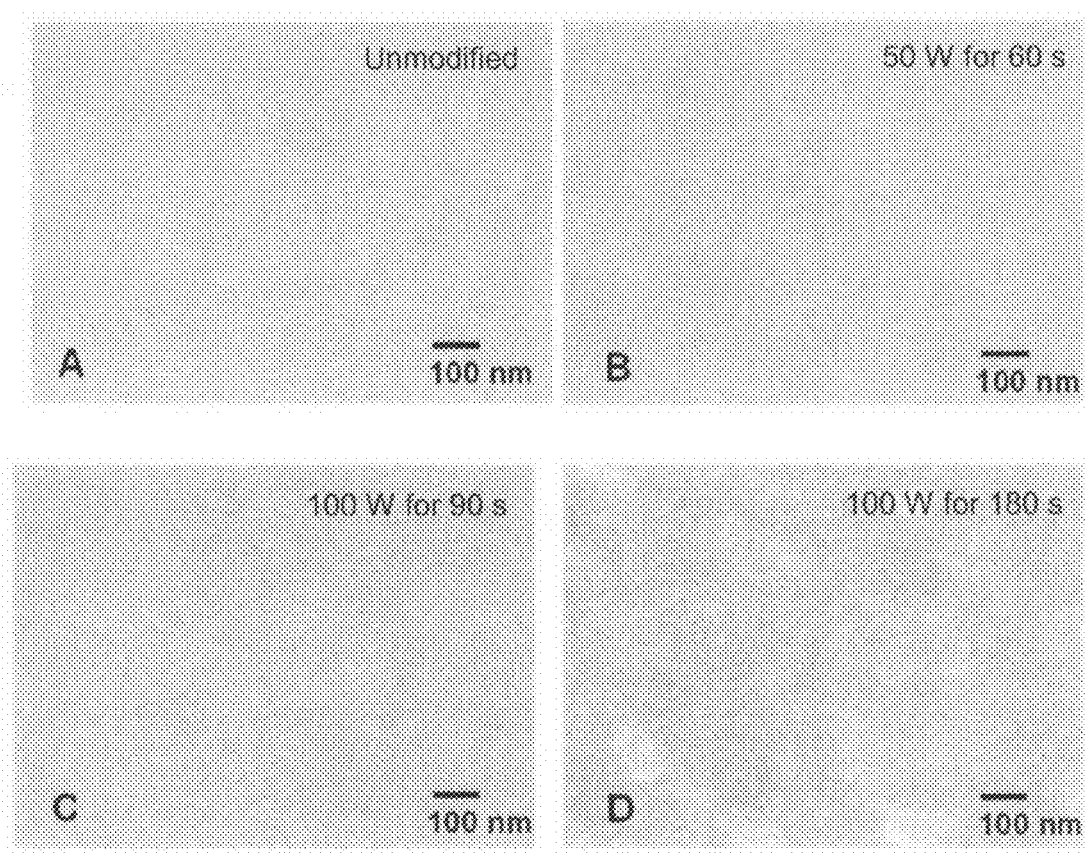
FIG. 2B illustrates SEM analysis of RFGD modified PMP hollow fiber membranes wherein the hollow fibers were exposed to water plasma over a range of powers and exposure times under a 400 mTorr vacuum, and the images were taken at 100,000 times magnification using an accelerating voltage of 10 kV, wherein slide (A) sets forth a micrograph of unmodified HFM, slide (B) sets forth a micrograph of HFM modified using a power and duration of 50 W and 60 s, respectively, slide (C) sets forth a micrograph of HFM modified using a power and duration of 100 W and 90 s, respectively, and slide (D) sets forth a micrograph of HFM modified using a power and duration of 100 W and 180 s, respectively.

To verify the effect of plasma treatment on the structural integrity of the fibers, various conditions of RFGD treated PMP HFMs (unmodified, 50 W for 60 s, 100 for 90 s, and 100 W for 180 s) were analyzed using SEM analysis as illustrated in FIG. 2B. SEM images of the RFGD modified fibers showed visual changes in the surface roughness of the samples. The RFGD treatment caused defects on the outer surface of the fibers in proportion to time and power. The sample treated at 100 W for 180 s exhibited significant surface damage, including cracking on the fiber (see FIG. 2B, slide D). The sample treated at 50 W for 60 s (FIG. 2B, slide B), however, exhibited a similar outer surface to a unmodified membrane (FIG. 2B, slide A).

Figure 3:
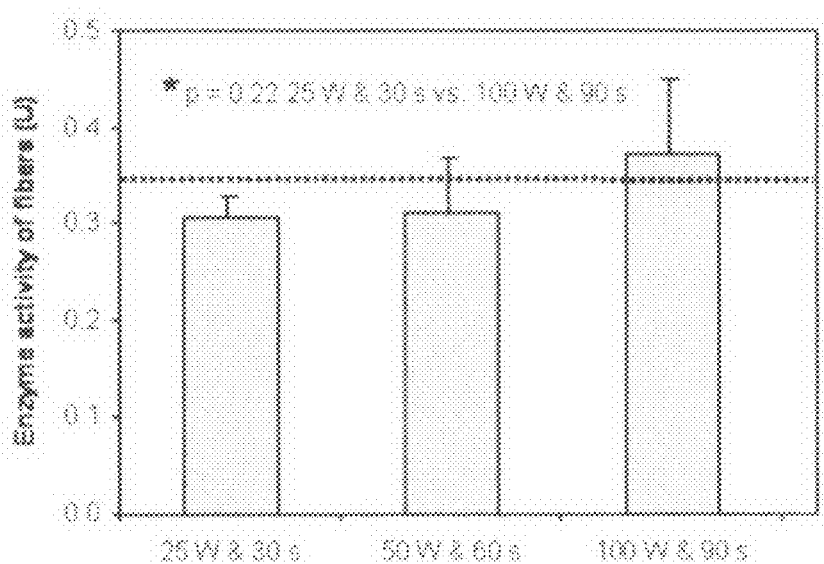
FIG. 3 illustrates a study of the effect of RFGD plasma deposition conditions on enzyme immobilization efficiency wherein the dashed line indicates the theoretical enzyme activity at monolayer CA coverage.

The enzyme activity on the HFMs as a function of CA loading for various conditions of RFGD treatment was evaluated as illustrated in FIG. 3. The immobilization efficiency of the sample treated at 25 W for 30 s, based on the enzyme activity assay, was lower than that of the sample treated at 100 W for 90 s. However, no statistical difference was observed between the two groups (p=0.22). Up to 88% functional CA coverage on the fiber surfaces was achieved using samples treated with RFGD at 25 W for 30 s. For the purposes of the present studies, it was concluded that treatment conditions of 25 W and 30 s were sufficiently optimized with regard to prevention of fiber damage and CA loading.

Figure 4:
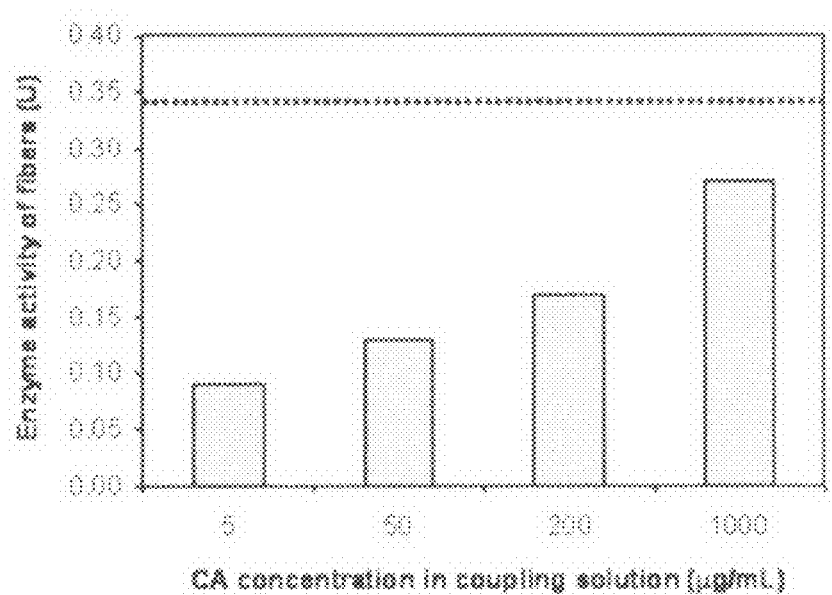
FIG. 4 illustrates a study of enzyme immobilization efficiency with varying CA concentration in the coupling solution wherein various levels of enzyme activity of the fibers as a function of CA loading were achieved, and the dashed line indicates the theoretical enzyme activity at monolayer coverage of CA on outer surface of the fibers.

The effect of CA concentration (5, 50, 200, and 1000 μg/mL) in a coupling solution on enzyme immobilization efficiency was also studied. Results demonstrated that enzyme activity (U) of the fibers as a function of CA loading was proportional to CA concentration. Fibers with 0.09, 0.13, 0.17, and 0.27 U were obtained as illustrated in FIG. 4 for CA concentrations of 5, 50, 200, and 1000 μg/mL, respectively. Additionally, the functional CA coverage on the fibers was determined by calculating the percentage of the actual enzyme activity on the fibers measured over the theoretical enzyme activity. The enzyme activity levels set forth above represent 26, 38, 50, and 79% of maximum theoretical activity of the fibers based on monolayer surface coverage of CA (2710 U of native enzyme used) on the outer surface of fibers.

In calculating, maximum theoretical activity based on a monolayer surface coverage, it was assumed that a single molecule of CA covers 44.5 nm$^2$ (6.67×6.67 nm). Saito et al. Acta Cryst. 2004. D60. 792-795. Thus, CA could be immobilized as much as 112 ng/cm in case of theoretical monolayer coverage. Thus, one can determine the amounts and % of CA immobilized through CA activity assay (esterase activity measurement). As, the surface area of the HFM used in the studies was 50 cm$^2$, the enzyme activity levels set forth above correspond to specific enzyme activities of 0.0018 U/cm$^2$, 0.0026 U/cm$^2$, 0.0034 U/cm$^2$ and 0.0054 U/cm$^2$. In general, specific enzyme activities of at least $1.5 \times 10^4$ U/cm$^2$ are readily achievable in the present invention. In a number of preferred embodiments, specific activity of membranes (for example, HFM) of the present invention is at least $1.5 \times 10^{-3}$ U/cm$^2$, or even at least $3.0 \times 10^{-3}$ U/cm$^2$, or even at least $5 \times 10^{-3}$ U/cm$^2$, or even at least $1.0 \times 10^{-2}$ U/cm$^2$.

The relationship between gas permeance and CA loading on the HFM was investigated. For the gas permeance tests results set forth in Table 1, $O_2$ as well as $CO_2$ were used as the gas source. In these tests, it was assumed that the gas permeance may be affected by immobilized CA when $CO_2$ is used as a gas source since $CO_2$ is a substrate of the CA immobilized on the outer surface of the HFM. Thus, $O_2$ was additionally chosen as an "inert" gas source, although $CO_2$ is a target test gas in gas exchange experiments. No relationship was observed between levels of covalently immobilized CA and gas permeance, regardless of gas source. This indicates that the CA was attached in a manner that does not impede diffusion of gas into the microporous fiber. Without limitation to any mechanism, this observations may be a result of the binding pattern of CA on the membrane surfaces. In that regard, the enzymes may be anchored on the outer surface of the fibers with micro, spot-like contact as even one covalent bond can be effective to immobilize ligand molecules. In other words, the contact area of the immobilized CA may be negligible compared to the total outer surface area of the fibers. This observation indicates that a higher level of CA immobilization is not a limiting factor in terms of the rate of gas exchange and that it can be beneficial to immobilize as much CA per unit surface area as possible to accelerate the rate of $CO_2$ removal from blood.

Table 1 sets forth data on the relationship between enzyme activity levels of the fibers obtained above (0, 0.09, 0.13, 0.17, and 0.27 U) and their gas permeance. Once again, the amount of CA immobilized onto the fiber surface had no effect on the gas permeance of the HFMs. Comparison of results for control samples (non-CA immobilized fiber that were, however, RFGD and CNBr activated) with the other samples showed no statistically significant difference regardless of gas source ($CO_2$ or $O_2$). The p values through Student t-test ranged between approximately 0.18-0.90 for $CO_2$ and between approximately 0.06-0.94 for $O_2$. The control had higher gas permeance than that of the intact (non-activated) fiber, but the difference was negligible (data for intact fiber are not shown). Statistical comparisons were performed using a Student's t-test assuming two-tailed data distribution and equal sample variance. The results of the gas permeance evaluation were analyzed using the above assumptions. In general, statistical significance was defined as p<0.05 in the studies of the present invention.

TABLE 1

Relationship between CA activity levels of the fibers as a function of CA loading and their gas permeance

| Test variables | Enzyme activity (U) | K (mL/s/cm$^2$/cmHg) | K (%) | p value |
|---|---|---|---|---|
| (1) For $CO_2$ as a gas source | | | | |
| 0 μg/mL CA | 0 | 1.64E–03 ± 1.83E–04 | 100 | — |
| 5 μg/mL CA | 0.09 | 1.82E–03 ± 7.71E–05 | 111 | *0.18 |
| 50 μg/mL CA | 0.13 | 1.62E–03 ± 7.07E–05 | 99 | **0.90 |
| 200 μg/mL CA | 0.17 | 1.78E–03 ± 9.68E–04 | 109 | †0.30 |
| 1000 μg/mL CA | 0.27 | 1.79E–03 ± 6.75E–05 | 109 | ‡0.24 |
| (2) For $O_2$ as a gas source | | | | |
| 0 μg/mL CA | 0 | 1.44E–03 ± 2.16E–04 | 100 | — |
| 5 μg/mL CA | 0.09 | 1.74E–03 ± 6.64E–05 | 120 | *0.08 |
| 50 μg/mL CA | 0.13 | 1.42E–03 ± 8.83E–05 | 99 | **0.94 |
| 200 μg/mL CA | 0.17 | 1.78E–03 ± 1.07E–04 | 124 | †0.07 |
| 1000 μg/mL CA | 0.27 | 1.79E–03 ± 7.14E–05 | 124 | ‡0.06 |

Figure 5:
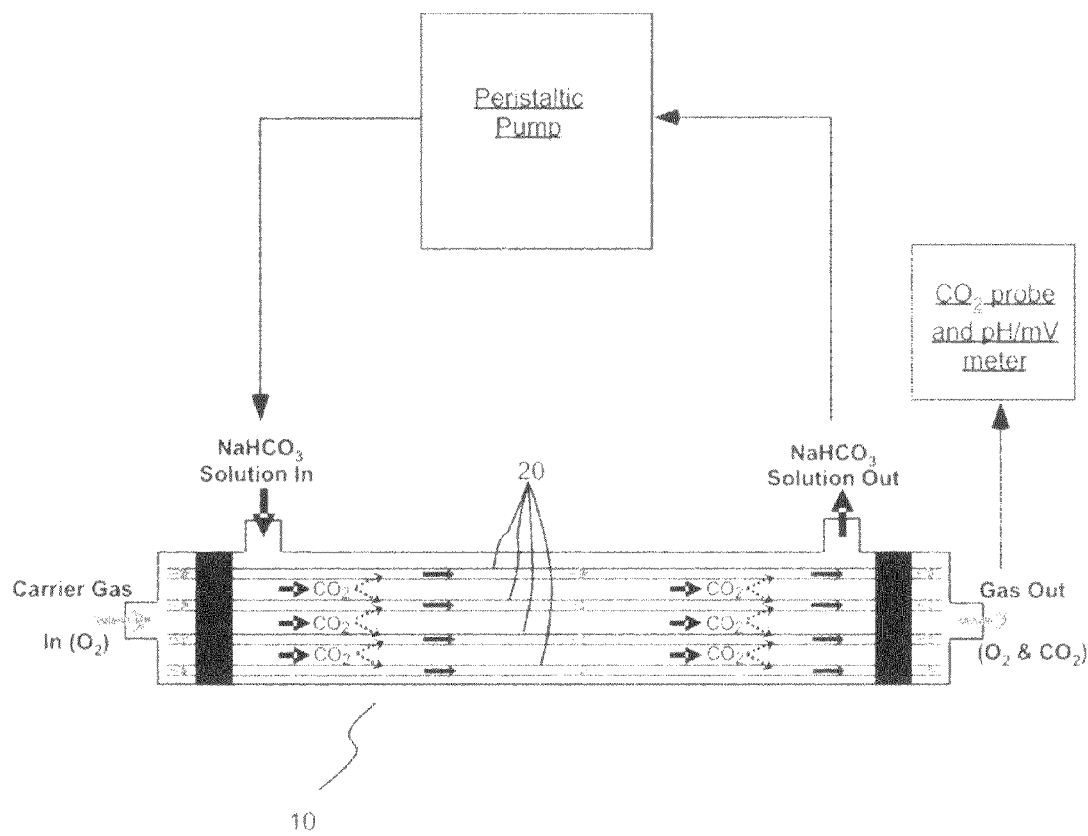
FIG. 5 illustrates an embodiment of a mini-lung and $CO_2$ removal measurement system of the present invention as used in several studies of the present invention.
Figure 6:
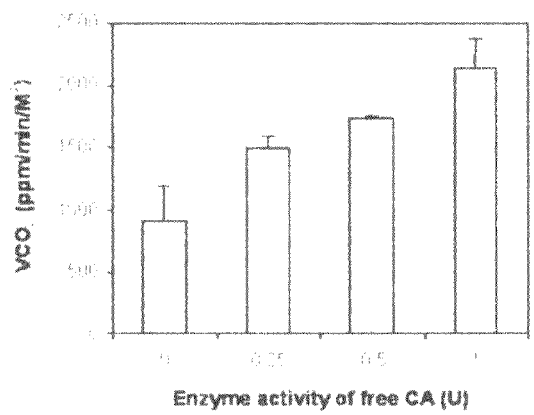
FIG. 6 illustrates an evaluation of $CO_2$ removal by adding various activities of free CA wherein the surface area of HFM was 71.6 $cm^2$ and wherein error bars denote the standard deviation (n=2).

**0 versus 5 μg/mL CA
***0 versus 50 μg/mL CA
†0 versus 200 μg/mL CA
‡0 versus 1000 μg/mLCA To evaluate the impact of CA on $CO_2$ removal performance, a $CO_2$ detection system was constructed including fabrication of an HFM mini-lung module 10 as illustrated in FIG. 5. $CO_2$ removal was first evaluated by adding free CA in the min-lung module 10 of FIG. 5 wherein the module contained unmodified fibers 20. The purpose of these experiments was to collect reference $CO_2$ removal data for various enzyme activity levels and to compare the removal efficiency with that obtained in experiments including fibers with immobilized CA. $CO_2$ removal was evaluated by adding various activities of free CA (0.25, 0.5, and 1 U in 25 mM $NaHCO_3$ solution using the mini-lung device containing unmodified HFMs. As illustrated in FIG. 6, the rate of $CO_2$ removal increased 1.71-, 2.09-, and 2.76-fold, respectively, compared to that of the control (no addition of CA). No physical adsorption of CA on the HFM was observed during each circulating procedure of free CA (data not shown). The results demonstrated that the $CO_2$ removal rate is a function of enzyme activity.

Figure 7:
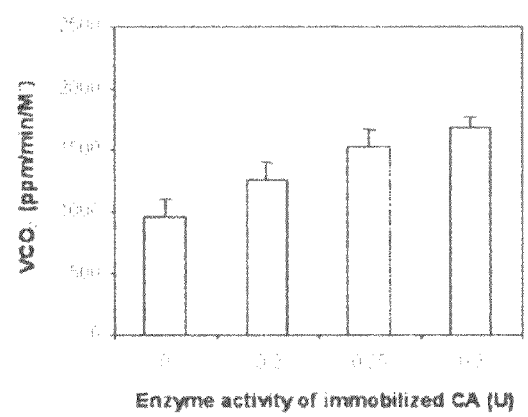
FIG. 7 illustrates an evaluation of $CO_2$ removal by immobilizing various enzyme activity levels of CA on HFM wherein the surface area of HFM was 74 $cm^2$ and wherein error bars denote the standard deviation (n=2) (CA test mini-lung module and others testing conditions were the same in the studies of FIGS. 6 and 7).

$CO_2$ removal for various enzyme activity levels of CA immobilized HFM was compared under a constant liquid flow rate (10 mL/min) and sweep gas flow rate (30 mL/min). As illustrated in FIG. 7, $CO_2$ removal in the mini-lung containing fibers with 0.2, 0.25, and 0.3 U of immobilized CA activity were improved by approximately 48%, 64%, and 75%, respectively. No enzyme desorption from the fibers was observed in these experiments (data not shown).

Figure 8:
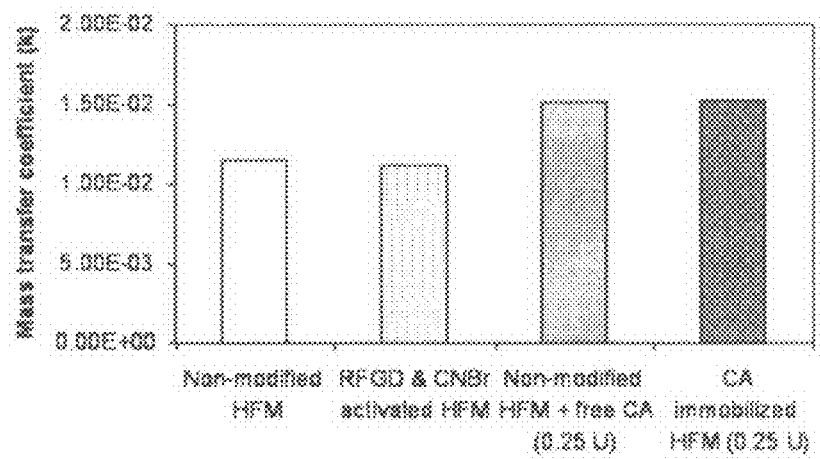
FIG. 8 illustrates a comparison of mass transfer coefficients for various fibers wherein the liquid flow rate and sweep gas flow rate in the mini-lung module were set at 10 mL/min and 30 mL/min, respectively.

FIG. 8 illustrates a comparison of mass transfer coefficient for various conditions of fibers. HFM that underwent RFGD and CNBr activation without enzyme modification did not exhibit changes in mass transfer coefficient as compared to unmodified HFM. The enzyme immobilized fibers showed similar mass transfer coefficients to an unmodified HFM module containing the same enzyme activity level of free CA (0.25 U).

The gas exchange efficiency for $CO_2$ removal using CA immobilized fibers was slightly lower than that of free CA, but the results were quite similar (see FIGS. 7 and 8). The efficiency of $CO_2$ exchange can be further improved by increasing the amount of immobilized enzyme activity on the fibers. A 3-dimensional immobilization of CA on the HFM can, for example, be used to significantly improve enzyme immobilization efficiency beyond monolayer attachment.

In that regard, the immobilization of CA onto cyanogens bromide-activated HFMs yields a single layer of enzyme on the fiber surface. As discussed above, one strategy to increase the amount of CA and thus the enzymatic activity on the fibers is to immobilize multiple layers of enzyme in a 3-dimensional immobilization. Bifunctional crosslinking agents such as glutaraldehyde, which reacts with primary amines, and EDC (1-ethyl-3-(3-dimethylaminopropyl)carbodiimide), which reacts with carboxylic acids, may be employed to conjugate additional CA to the surface-immobilized CA. Successive crosslinking steps will ultimately result in the formation of a multilayer CA shell with activity enhancements potentially several fold greater than achieved with the current model.

Figure 9A:
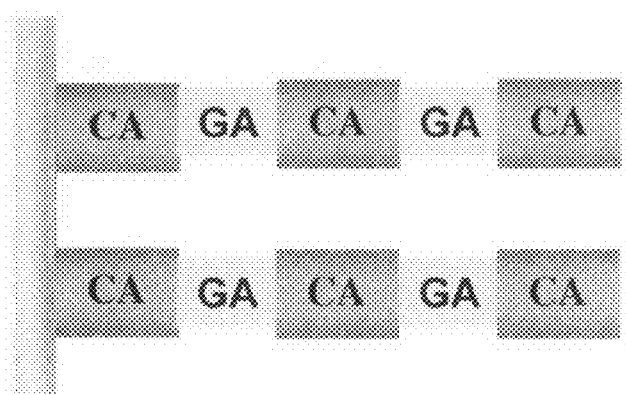
FIG. 9A illustrates a schematic representation of layer-by-layer CA assembly using a glutaraldehyde chemistry in which glutaraldehyde (having two aldehyde end groups) was used to covalently cross link between amine containing molecules such as CA and PLL in which CA was first immobilized.
Figure 9B:
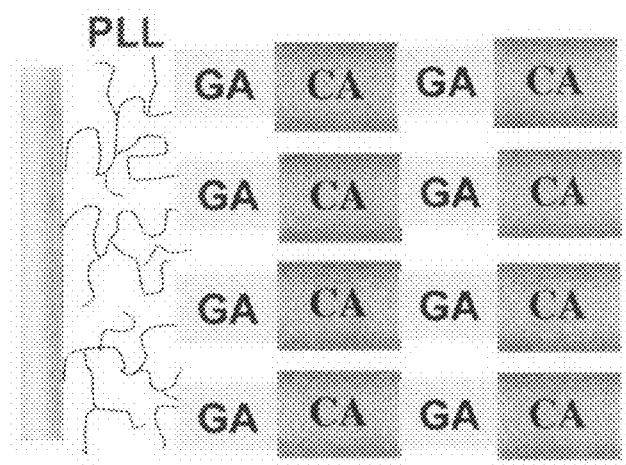
FIG. 9B illustrates a schematic of layer-by-layer CA assembly using a glutaraldehyde chemistry in which glutaraldehyde was used to covalently cross link between amine containing molecules such as CA and PLL in which PLL was first immobilized.
Figure 9C:
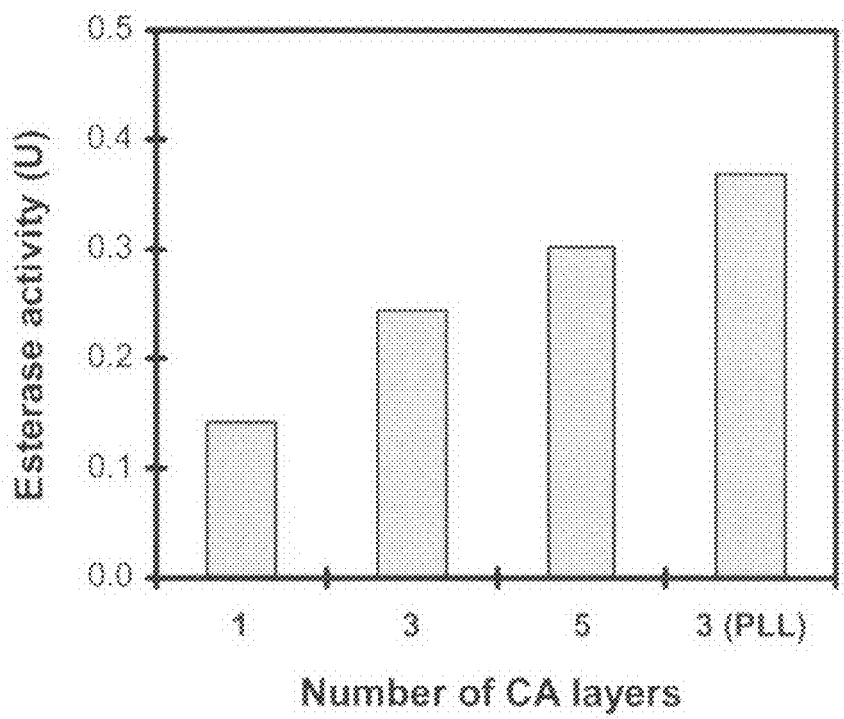
FIG. 9C illustrates graphically increases in esterase activity resulting from increasing number of CA layers deposited on HFM surface.

In several studies, CA loading was increased by immobilizing multiple enzyme layers on the surface of HFM as discussed above. FIG. 9A sets forth a schematic representation of the layer-by-layer assembly of surface immobilized CA in which glutaraldehyde is used as a cross-linking agent. CA was initially immobilized on the HFM using the general procedure previously outlined. The CA-immobilized HFM were subsequently immersed in a 0.5% (v/v) glutaraldehyde solution for 30 min with mild shaking at room temperature, resulting in the modification of free primary amines on the enzyme surface. Any non-covalently attached glutaraldehyde was removed from the HFM surface by thorough rinsing of the HFM with deionized water. The glutaraldehyde-treated HFM were then reacted with CA at a concentration of 1 mg/mL in buffer (50 mM phosphate, pH 7.5) for 1 hr. In this way, primary amines in the enzyme, such as the E-amine on the side chain of lysine residues or the N-terminal α-amine, will react with the remaining free aldehyde functional group of glutaraldehyde, forming a second layer of CA. The two step process of glutaraldehyde treatment and subsequent reaction with additional enzyme was repeated to assemble up to 5 layers of enzyme on the surface of HFM (see FIG. 9A). Increases of 71% and 112% in esterase activity were measured for HFM with 3 and 5 layers of immobilized CA respectively relative to HFM modified with monolayer CA coverage (FIG. 9C).

As clear to one skilled in the art, use of multiple layers of immobilized CA can result in enzyme activity greater than the maximum theoretical activity based upon monolayer surface coverage. In general, activity resulting from multiple layers is additive as compared to a corresponding single layer.

The loading of CA onto surface of HFMs was also be increased by initially modifying the surface of HFM with poly-L-lysine (PLL; $M_w$ 70-150 kDa), which in effect introduces additional reactive sites for CA immobilization. Using this approach, PLL was initially immobilized onto plasma-activated HFM that had been reacted with CNBr. The PLL-modified HFM were reacted with glutaraldehyde and subsequently with CA as described above. Successive treatments of glutaraldehyde and CA were applied to add additional layers of immobilized CA (see FIG. 9B). CA loading was improved by 159% by constructing 3 layers of immobilized CA onto HFM compared to CA-immobilized HFM prepared with the standard method (see FIG. 9C).

In the use of HFM including immobilized CA in artificial lung systems for clinical use, it can also be beneficial to protect the enzyme from proteases in blood. Such protection can, for example, be achieved by modification of the enzyme such as a PEGylation to maintain enzyme activity. In that regard, covalent binding of polyethylene glycol (PEG) to enzymes is known to improve stability.

Proteolytic degradation of the immobilized CA and nonspecific binding between CA and plasma proteins may reduce the catalytically active half-life of the CA-modified HFMs upon exposure to circulating blood. In general, many therapeutic enzymes are stable for times on the order of only minutes to hours as a result of physiological clearance mechanisms. One approach to prolonging the bioactivity of the fibers is to covalently attach poly(ethylene glycol) (PEG) to the surface of the immobilized enzyme. When conjugated to an enzyme, the PEG chains form a fluid barrier that via steric effects blocks interactions with other proteins. PEG-protein conjugates are readily synthesized by reacting activated PEGs with functional groups such as amines or thiols on the side chain of amino acids. In the case of the modified HFMs, the CA can be PEGylated before or after immobilization onto the fiber surface. Additionally, by blocking the adsorption of plasma adhesive proteins such as fibrinogen, PEGylation of the immobilized CA may prevent thrombotic deposition on the fiber surface. As set forth in platelet activation studies discussed below, the enzyme itself seems to assist in preventing thrombotic deposition on the fiber surface. The adhesion of platelets, which can lead to acute thrombosis on blood-contacting biomaterials, may potentially block diffusion of $CO_2$ through the HFMs. See, for example, Xu H., Kaar J L, Russell A J, Wagner W R. Characterizing the modification of surface proteins with poly(ethylene glycol) to interrupt platelet adhesion. *Biomaterials* 2006; 27,3125-3135.)

Figure 10A:
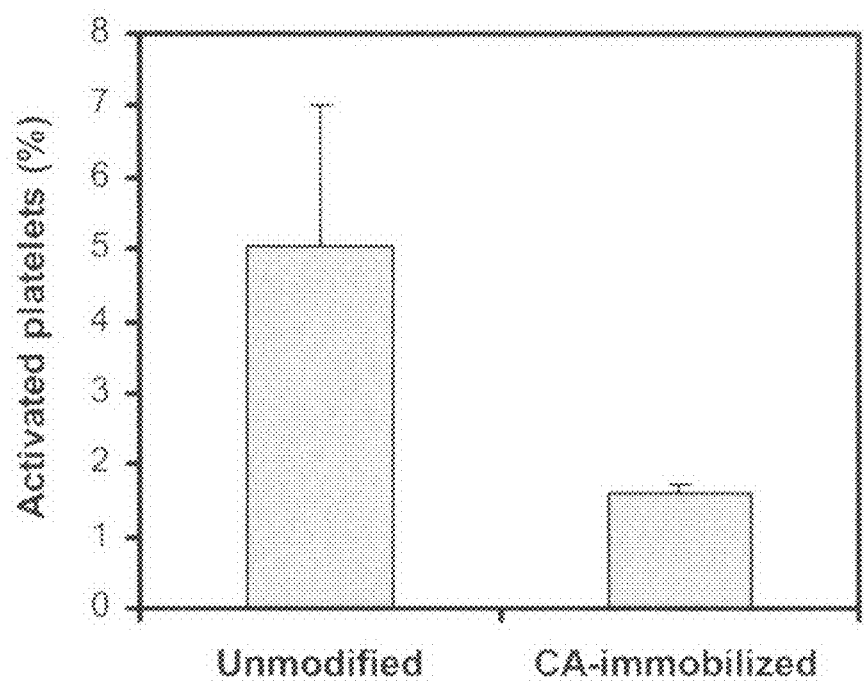
FIG. 10A illustrates quantification of activated platelet by flow cytometry using annexin V as a marker.
Figure 10B:
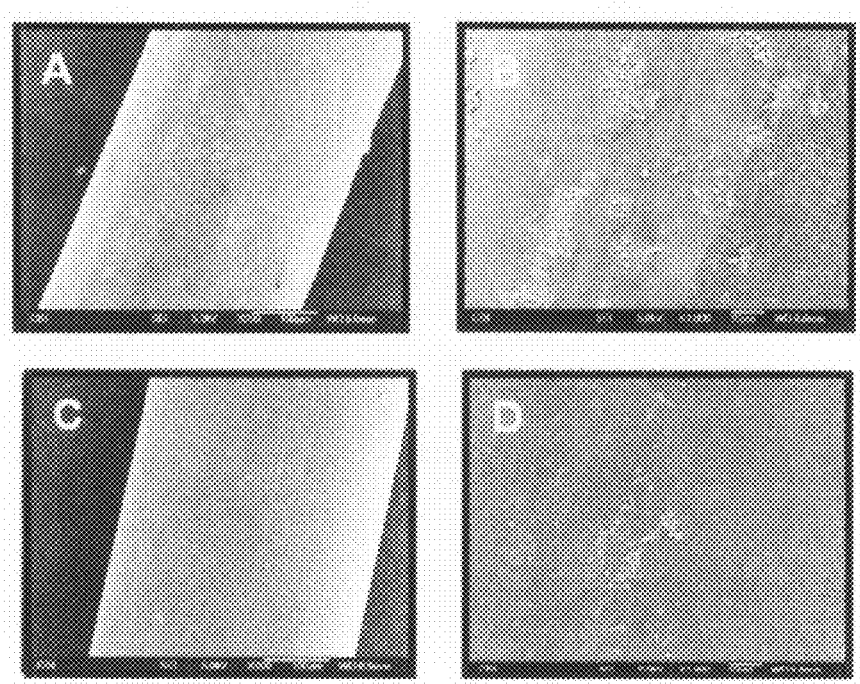
FIG. 10B illustrates a comparison of activated platelet adhesion by SEM in which slides A and B illustrate unmodified hollow fiber membranes and slides C and D illustrates CA-immobilized hollow fiber membranes at ×200 and ×1000 magnification, respectively.

The biocompatibility of CA-immobilized HFM was assessed using a platelet activation assay. Whole sheep blood, containing 6 unit/mL of heparin, was incubated with CA-immobilized and unmodified HFM for 2 hrs with mild shaking at 37° C. At the end of the incubation step, the relative fraction of activated platelets in the blood was quantified by flow cytometry using the protein annexin V as a marker. Results of the assay indicated that the immobilization of CA significantly reduced platelet activation (see FIG. 10A, $p<0.05$). Additionally, the degree of platelet deposition onto the surface of the CA-immobilized and unmodified HFM was observed by SEM. Images of CA-immobilized HFM showed considerably less platelet deposition than in images of unmodified HFM (FIG. 10B).

The impact of immobilized CA on $CO_2$ removal from bovine blood was determined using a model respiratory assist device comprised of a bundle of single layer CA-immobilized HFM similar to that illustrated in FIG. 5. The blood contacting membrane area in the device was 83.57 cm². Fresh blood (40 mL) was perfused around the fibers at a rate of 150 mL/min while the flow rate of sweep gas was set at 150 mL/min. A blood gas analyzer (Radiometer America, ABL 555, Westlake, Ohio) was used to monitor the amount of $CO_2$ in the blood every 2.5 min over the course of 10 mins. The rate constant for $CO_2$ removal was determined by using modified $CO_2$ dissociation curve equation as follows:

$$TCO_2 = apCO_2^b \quad (1)$$

where $TCO_2$ represents the total $CO_2$ (volume %) and $pCO_2$ is the partial pressure of dissolved $CO_2$ (mmHg).

A mass balance on the blood volume in the model device yields:

$$d/dt[TCO_2] = kApCO_2 \quad (2)$$

where k is the mass transfer coefficient and A is the membrane surface area.

Substituting into equation 1:

$$abpCO_2^{b-1} d/dt[pCO_2] = kApCO_2 \quad (3)$$

Integrating equation 3 results in:

$$pCO_2(t)^{m*} - pCO_2(t_0)^{m*} = K*t \quad (4)$$

where $pCO_2(t)$ and $pCO_2(t_0)$ represent $pCO_2$ values at designated monitoring time (0, 2.5, 5, 7.5, and 10 min) and zero time, respectively, $m*$ is equal to $b-1$, and $K*$ is equal to $k(b-1)A/a\,b$ which represents the $CO_2$ removal rate constant. The $CO_2$ removal rate constant is directly proportional to the mass transfer coefficient, k, dictating $CO_2$ removal as per eq 2.

Figure 11A:
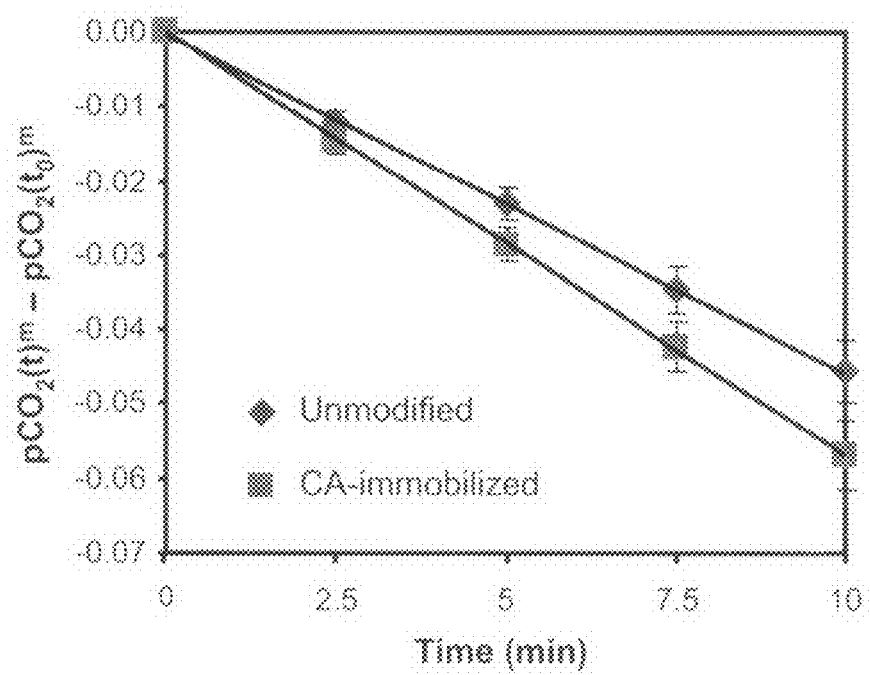
FIG. 11A illustrates $CO_2$ removal from bovine blood using unmodified and CA-immobilized hollow fiber membranes in the mini-lung (passive mixing) system similar to that of FIG. 5.
Figure 11B:
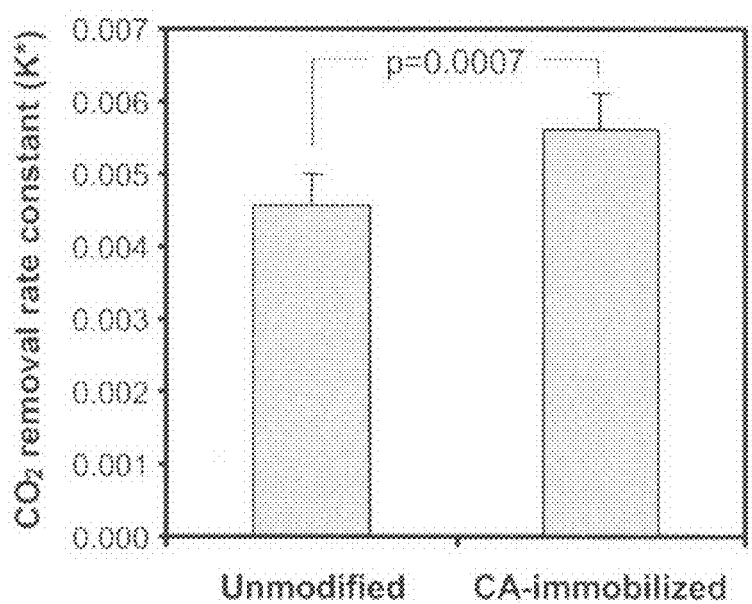
FIG. 11B illustrates rate constants for unmodified hollow fiber membranes and CA-immobilized hollow fiber membranes in removal of $CO_2$ from bovine blood, wherein the rate constants shown are linearly proportional to mass transfer coefficients for removal from blood.

The non-optimized results of several studies showed that the rate of $CO_2$ removal with CA-immobilized HFMs was improved by, for example, 10-30% compared to unmodified HFM (FIGS. 11A and 11B).

Figure 12A:
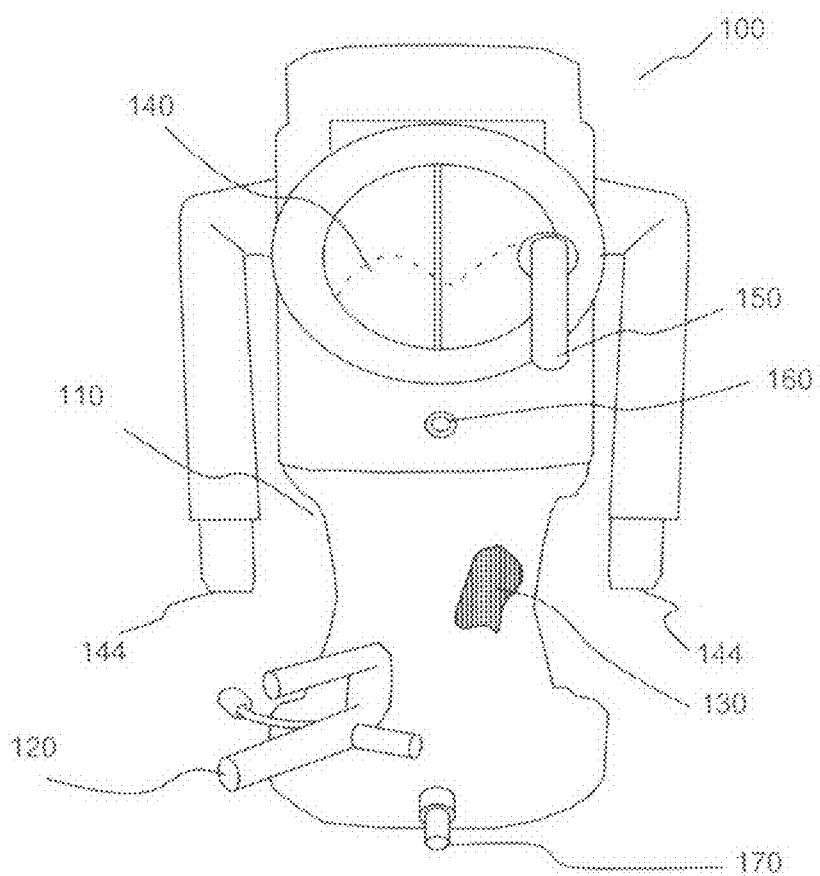
FIG. 12A illustrates a partially cutaway view (wherein a portion of the housing is cutaway to show the HFM therein) of an embodiment of a commercially available artificial lung into which HFM including immobilized CA of the present invention can be incorporated.

FIG. 12A illustrates an embodiment of a commercially available artificial lung device 100 including a housing 110 into which HFM including immobilized CA of the present invention can be incorporated or retrofitted. The most common artificial lungs are the blood oxygenators used in cardiopulmonary bypass circuits, and examples include, but are not limited to, the CAPIOX® SX available from Terumo Cardiovascular Systems, the QUODROX® available from Jostra, and the AFFINITY®, available from Medtronic.

Figure 12B:
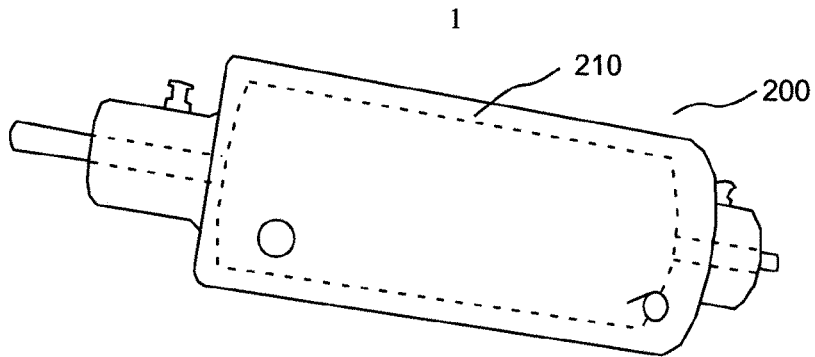
FIG. 12B illustrates an embodiment of a paracorporeal respiratory assist lung (PRAL) of the present invention in an assembled state.
Figure 12C:
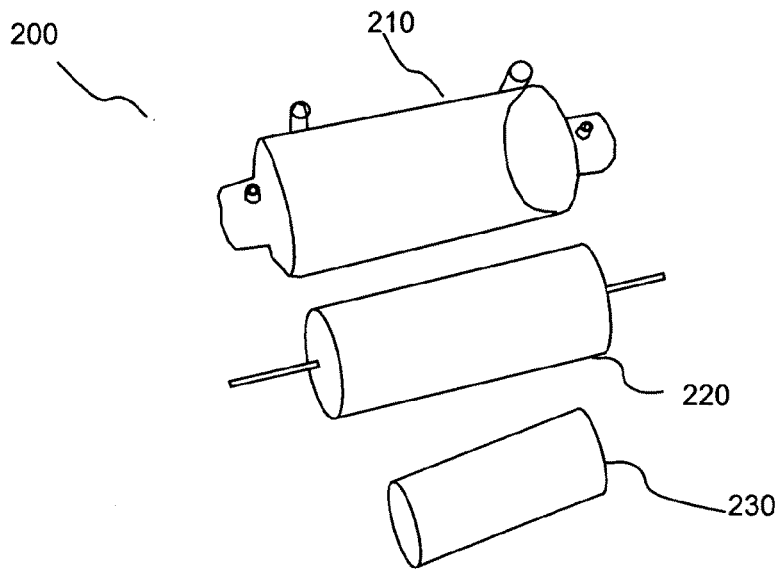
FIG. 12C illustrates the paracorporeal respiratory assist lung of FIG. 9B in a disassembled state.

In addition to use in these commercially available oxygenators, HFM including immobilized CA of the present invention can also be incorporated into artificial lungs being developed as respiratory assist devices. As used herein, the term artificial lung includes respiratory assist devices. These devices include total artificial lungs (TALs) being developed as bridge to lung transplant devices as well as respiratory assist devices being developed for acute lung failure or acute-on-chronic lung failure. FIGS. 12B and 12C illustrate an embodiment of a paracorporeal respiratory assist lung (PRAL). The device of FIGS. 9B and 9C uses hollow fiber membranes that are rotated to improve gas exchange and also to pump blood.

Most blood oxygenators or respiratory assist devices are artificial lungs that include either microporous polypropylene hollow fiber membranes or, as in some design, silicone sheets. The general anatomy of oxygenators and respiratory assist devices are similar between the two types of devices and are even similar between fiber membrane versus sheet membrane devices despite the differing gas exchange surfaces. Referring to device 100 of FIG. 12A, blood enters oxygenator 100 through an inlet port 120 and flows either along the outside of hollow fibers 130 or the outside of the silicone sheet. The blood is then collected in a manifolded region, flows through a heat exchanger 140, and then exits the device through an outlet port 150. Water of other fluid port 144 can be provided in connection with heat exchanger 140. The gas, which can be pure oxygen or a mixture of oxygen and room air, enters oxygenator 100 through a gas inlet port 160, flows through the inside of the hollow fibers/silicone sheets 130, and exits the device via an outlet port 170t.

Figure 12D:
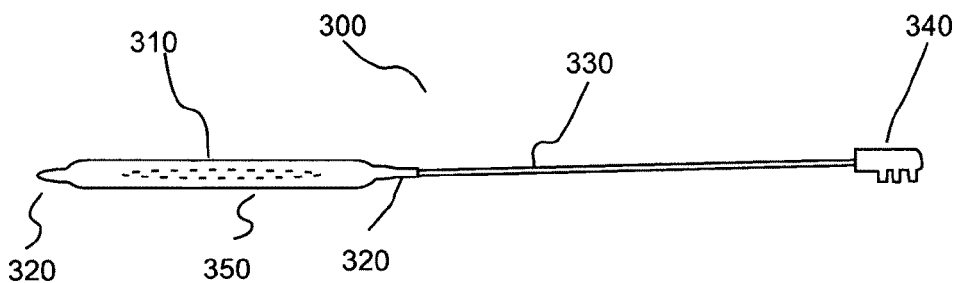
FIG. 12D illustrates an embodiment of a intravascular respiratory assist catheter of the present invention.

Important design considerations in blood oxygenators include minimizing the resistance to blood flow, reducing the priming volume, ensuring easy debubbling at setup, and minimizing blood activation and thrombogenicity. Most currently available blood oxygenators have fiber membranes with outer diameters of approximately 200-400 microns and wall thickness of approximately 20-50 microns, total membrane surface area of approximately 2-4 m², and blood priming volume of approximately 135-340 ml. The hollow fibers are, for example, wound or matted within a hard plastic outer shell to produce fiber packing densities in the bundle of approximately 40-60%, and the arrangement of the fiber bundle and blood flow patterns differ between devices. For example, fibers are helically wound in the Medtronic AFFINITY NT oxygenator. Blood enters the device through a central core channel and is then distributed radially through the fiber bundle. Fibers in the Jostra QUODROX oxygenator are, for example, aligned so that blood flow is perpendicular to the gas pathways. Hollow fiber oxygenators with intraluminal blood flow have been designed but are used less often because of a generally unfavorable high resistance to blood flow and inferior gas exchange efficiency (gas exchange per membrane area). Respiratory assist devices may use less fiber membrane surface area than commercial blood oxygenators either because gas exchange requirements are less or because the devices incorporate special features that improve the rate of gas exchange per unit fiber surface area. An example is the rotating fiber bundle of PRAL 200 of FIGS. 12B and 12C developed for acute respiratory support. PRAL 200 includes an outer housing 210, a fiber bundle system 220 and a stationary inner core 230. Another type of artificial lung being developed that can use HFMs with immobilized CA of the present invention is an intravascular respiratory assist catheter. FIG. 12D illustrates an example of such a device 300, which is, for example, designed for placement within the large veins returning blood to the heart. Intravascular respiratory assist catheter 300 does not have plastic housings incorporating fiber bundles 310, as such fiber bundles 310 are designed to be floating within a blood vessel while manifolded via manifolds 320 and connected through tubing 330 (via an external connector 340) to a gas supply source outside the body. An expandable balloon 350 is placed internal to fiber bundle 310. Designs can also use mixing impellers in the place of balloons to enhance gas exchange.

Silicone membrane oxygenators are often used in extracorporeal membrane oxygenation for respiratory support since plasma leakage does not occur as can occur in microporous hollow fiber oxygenators. A spiral-wound silicone membrane oxygenator contains two silicone sheets sealed around the edges, which are wound around a polycarbonate core. Gas flows within the sealed sheets and blood flows countercurrently between the spiral wraps. The surface area of silicone membrane oxygenators ranges from approximately 0.4 to 4.5 $m^2$ and the priming volumes range from approximately 90 to 665 ml. Because diffusion occurs across a nonporous silicone sheet, the thickness of these sheets was reduced to approximately 100-200 μm. Nevertheless, the gas exchange efficiency of silicone oxygenators is substantially below that of hollow fiber oxygenators. The Avecor 0800 silicone oxygenator, for example, has an $O_2$ transfer efficiency of 88 ml/min/$m^2$ compared to 150 ml/min/$m_2$ for the AFFINITY hollow fiber device and 250-500 ml/min/m2 for the respiratory assist devices shown in FIGS. 12B and 12D. The resistance to blood flow is also higher in silicone sheet oxygenators than in hollow fiber oxygenators, and debubbling the sheet oxygenators can be more difficult.

As discussed above, CA can be immobilized on a wide variety of polymeric materials, including, but not limited to, microporous hollow fiber membranes and silicone sheets as described above. Hollow fiber membranes in artificial lungs (blood oxygenators or respiratory assist devices) are typically made using polyolefin polymers, with polypropylene, polyethylene and polymethylpentene being commonly used materials. The hollow fiber membranes are created by extrusion or other manufacturing processes to create a microporous fiber wall with sub-micron sized pores spanning the walls. These microporous fibers are adequate in commercial blood oxygenators for short term blood contact. In respiratory assist devices and artificial lungs required for longer-term blood contact (>6 hours), the microporous fibers can leak plasma into the fiber lumens and create a problem known as plasma wetting. To prevent or retard plasma wetting, composite or asymmetric microporous hollow fiber membranes have been developed. A composite HFM is a standard microporous hollow fiber membrane on which a thin coating of a nonporous (dense) polymer is applied. FIGS. 13A and 13B illustrate cross section views of HFMs with and without a nonporous coating, respectively. FIGS. 13C and 13D illustrate scanning electron micrographs of HFMs with and without a nonporous coating, respectively. As the nonporous coating polymers need to be very gas permeable the coating is often made from siloxane polymers. An asymmetric microporous hollow fiber membrane is one in which the fiber wall is fabricated so that the porosity varies across the wall and goes to zero at the fiber surface. The pores are then essentially sealed by the same material from which the fiber is made. FIG. 14 illustrates a scanning electron micrograph of an HFM fabric in which woven support threads are used to connect the hollow fibers. Once again, the CA immobilization techniques of the present invention can be used in connection with composite HFM, asymmetric HFM, HFM fabric, silicone sheets and many other polymeric and other surfaces.

Figure 15:
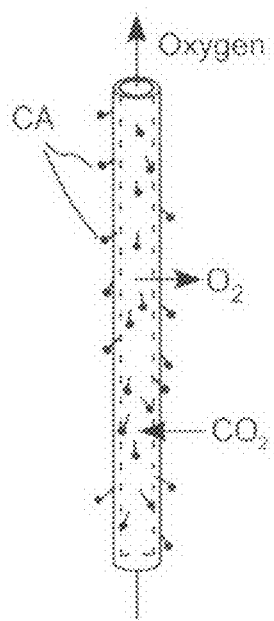
FIG. 15 illustrates an idealized representation of a hollow fiber upon which carbonic anhydrase has been immobilized upon the outer surface of the hollow fiber, and wherein oxygen passes from the lumen of the hollow fiber to blood on the exterior of the fiber and carbon dioxide passes from the blood on the exterior of the hollow fiber to the lumen of the hollow fiber.
Figure 16:
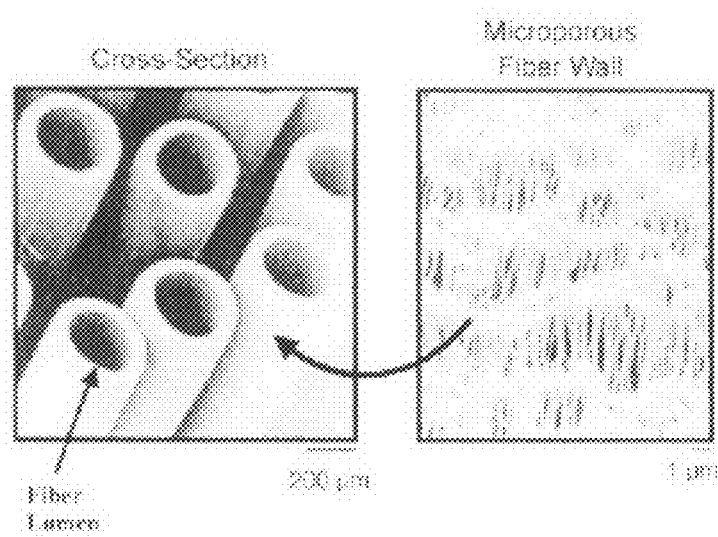
FIG. 16 illustrates scanning electron micrographs of microporous hollow fiber membranes suitable for use in artificial lungs wherein the walls of the fibers (right) contain submicron pores through which respiratory gases diffuse.

FIG. 15 illustrates an idealized representation of a hollow fiber upon which carbonic anhydrase has been immobilized upon the outer surface. As illustrated oxygen passes from the lumen of the hollow fiber to blood on the exterior of the fiber and carbon dioxide passes from the blood on the exterior of the hollow fiber to the lumen of the hollow fiber. FIG. 16 illustrates scanning electron micrographs of microporous hollow fiber membranes suitable for use in artificial lungs wherein the walls of the fibers (right) contain submicron pores through which respiratory gases diffuse.

Such fibers and other materials upon which CA has been immobilized as described herein can be used in other modules or devices designed to remove $CO_2$ from fluids (for example, liquids, gases and combinations thereof) in which a component of the $CO_2$ is in the form of bicarbonate ion. The liquids can also include CA in solution to facilitate the conversion of $CO_2$ to $HCO_3$ and $HCO_3^-$ to $CO_2$. Several examples include, but are not limited to, liquids used in total liquid ventilation, in which lungs are ventilated with oxygen carrying liquids like perfluorocarbons. These liquids are part of a closed circuit and, hence, $CO_2$ should be eliminated effectively from the liquids before they are pumped back into the lungs. Another potential application is in systems using peritoneal or gastric perfusion to provide respiratory support. Similar to liquids used in total liquid ventilation, the liquids used in peritoneal or gastric perfusion require an effective means to eliminate $CO_2$ before being pumped back into respective body compartments.

Further, it is not necessary that the CA be immobilized upon the surface through which gas diffusion/flow takes place. In the case of removal of $CO_2$ from blood, such a secondary surface upon which CA is immobilized is preferably in close proximity to the surface (for example, HFM) through which gas flow occurs. Preferably, the secondary surface is within approximately 50 μm of the gas diffusion membrane. More preferably, the secondary surface is within approximately 10 to 30 μm of the gas diffusion membrane. CA can, for example, be immobilized upon support threads that are used to connect the hollow fibers as illustrated in FIG. 14.

EXPERIMENTAL EXAMPLES

Materials. Carbonic anhydrase (CA) from bovine erythrocytes was purchased from Sigma-Aldrich (St. Louis, Mo.)

and used without further purification. Polymethyl-pentane (PMP) hollow fiber membranes (Oxyplus, Type PMP 90/200, OD: 380 μm, ID: 200 μm) were obtained from Membrana GmbH (Wuppertal, Germany). All other reagents were purchased from Sigma-Aldrich (St. Louis, Mo.) and were of analytical grade or purer.

CA Immobilization. PMP HFMs (Oxyplus, Type PMP 90/200, OD: 380 μm, ID: 200 μm) were used as the substrate for CA immobilization. Initially, the HFMs were treated by RFGD (GCM-250, March Plasma Systems, Concord, Calif., see FIG. 9L) using water as a plasma source. A range of plasma discharge powers (25, 50, and 100 W) and treatment time (30, 60, 90, and 180 s) were employed.

After RFGD treatment, the modified fibers were immersed in a 2 M $Na_2CO_3$ solution (no pH adjustment). CNBr (1 g/mL in acetonitrile) was added to the buffer solution to a final concentration of 100 mg/mL in which the fibers were incubated for 10 min with mild shaking. The fibers were subsequently washed extensively with ice-cold deionized water and coupling buffer (0.1 M $Na_2CO_3$, pH 8.0). Conjugation of CA to the CNBr-activated fibers was initiated by adding the fibers to coupling buffer containing 1 mg/mL CA. The reaction mixture was incubated for 3 hr after which any loosely adsorbed CA was removed by washing three times with phosphate buffer (50 mM, pH 7.5).

CA Activity Assay. The catalytic activity of CA was assayed using p-nitrophenyl acetate (p-NPA) as the substrate as described by Drevon et al. (2003). The mechanism of catalysis is believed to be the same for the dehydration of $HCO_3^{-1}$ and hydrolysis of p-NPA. Pocker Y, Sarkanen S. 1978. Carbonic anhydrase: structure, catalytic versatility, and inhibition. Adv Enzymol 47:149-274 and Pocker Y, Storm D R. 1968. The catalytic versatility of erythrocyte carbonic anhydrase. IV. Kinetic studies of the enzyme-catalyzed hydrolyses of p-nitrophenyl esters. Biochemistry 7:1202-1214. Briefly, p-NPA substrate dissolved in acetonitrile (40 μL, 40 mM) was added to different concentrations of CA (4 mL) prepared fresh in phosphate buffer (50 mM, pH 7.5). Enzyme activity was measured spectrophotometrically using a Genesys 5 UV spectrophotometer (Thermo Spectronic, Somerset, N.J.) by monitoring the hydrolysis of p-NPA to p-nitrophenol (p-NP) at 412 nm. Absorbance measurements were recorded every 1.5 min over the course of 6 min and plotted as a function of time. The molar extinction coefficient of p-NP (11.69 $cm^{-1}$ $mM^{-1}$) was measured and used to calculate enzyme activity. One activity unit was defined as the amount of enzyme that generates 1 μmol p-NP per minute.

The activity of CA immobilized on fiber membranes was measured using a method similar to that employed for assaying free CA. CA immobilized HFMs were cut into 1-2 mm segments and placed in a beaker (20 mL volume size) to which assay buffer (50 mM phosphate buffer, pH 7.5) was added (4 mL). The solution was mixed vigorously using a magnetic stirrer and the reaction was initiated by addition of the substrate (40 μL). To measure the absorbance, the solution was filtered and transferred to a cuvette using a syringe (BD, Franklin Lakes, N.J.) equipped with a syringe filter (PCG Scientific, Gaithersburg, Md.). The absorbance was measured at 3 min intervals over the course of 12 min.

Determination of Gas Permeance. The gas permeance of each fiber tested was measured using the method of Eash et al. (2004). Briefly, each fiber sample was fixed in nylon tubing. One end of the hollow fiber was occluded with glue and the other end of the hollow fiber was open to the gas outlet pathway. The tube inlet was connected to a gas source from which the flow of either $CO_2$ or $O_2$ was controlled via a pressure regulator. Gas permeance across the fiber membrane was determined as a function of the differential pressure between the gas inlet and outlet extending from the lumen of the fibers using a pressure transducer (SenSym Inc., Milpitas, Calif.). Gas flow rate was measured using a bubble flow meter (Supelco, Bellefonte, Pa.). Room temperature and atmosphere pressure was also recorded for the calculation of gas permeance. Gas permeance across the hollow fiber membrane was calculated using the following equation:

$$K = \frac{Q}{S \cdot \Delta P}$$

where K represents the gas permeance (mL/s/$cm^2$/cmHg), Q is the measured gas flow rate (mL/s), S is the calculated surface area of fiber exposed to test gas ($cm^2$), and $\Delta P$ is the differential pressure across the fiber wall (cmHg).

SEM Analysis of Hollow Fiber Membranes. RFGD plasma modified PMP HFMs were analyzed using SEM (JSM-6330F, JEOL, Peabody, Mass.) to characterize the outer surface of the membranes. Prior to analysis, the specimens were coated with a 3.5 nm gold/palladium layer to conduct electricity using a sputter coater (Cressington Auto 108, Cressington, Watford, U.K.). The samples were then placed inside the vacuum column of the instrument through an air-tight door. Images were taken at 100,000 times magnification using an accelerating voltage of 10 kV.

Assessment of $CO_2$ Removal in a Mini-Lung Module. Mini-lung modules were fabricated containing either modified or unmodified HFMs to compare the impact of CA-immobilization on the efficiency of $CO_2$ removal. Briefly, unmodified or CA-immobilized fibers (60 fibers, 10 cm) were inserted into a tubular module and fixed at both ends with an epoxy adhesive. The loose ends of the fibers at the fixing point were cut off. Inlet and outlet ports on the module allowed for the continuous flow of sodium bicarbonate buffer (2 mg/mL, pH 7.5), which was controlled by a peristaltic pump (MasterFlex C/L, Cole Parmer, Vernon Hills, Ill.). The flow of buffer was circulated in a closed loop with a maximum capacity of 10 mL such that the amount of $CO_2$ in the apparatus was tightly controlled. Two ¼"×¼" single luer locks (Qosina, Edgewood, N.Y.) were attached to the ends of the module serving as ports for the flow of sweep gas through the lumen of the fibers. Using tygon tubing (ID: 0.1099"), one end of the module was connected to a gas cylinder from which the flow of gas was controlled with a pressure regulator while the other end of the module was connected to a bubble flow meter. The residual concentration of $CO_2$ in the circulating buffer was monitored potentiometrically over time using a Analytical Sensor Instruments (Sugar Land, Tex.) CO 35 model $CO_2$ electrode and a Corning (Corning, N.Y.) 314 pH/Temperature Plus pH/mV meter (see FIG. 5).

In all experiments, pure oxygen was used as the sweep gas. The flow rate of the sodium bicarbonate buffer and sweep gas were set at 10 and 30 mL/min respectively. Fibers with a range of immobilized CA activity (0, 0.20, 0.25, 0.30 U) were employed. Experiments in which free CA (0, 0.25, 0.50, 1.00 U) was added to the module containing unmodified fibers were also performed. For these experiments, free enzyme was injected directly into the outer shell compartment of the mini-lung module after a stable $CO_2$ measurement was reached. To accurately measure the reduction of $CO_2$ in the closed loop system, total $CO_2$ rather than only dissolved $CO_2$, which is in equilibrium with the conjugate bicarbonate species ($HCO_3^-$) was measured. Samples were removed every 10 mins over a period of 30 mins and diluted ten-fold in a dilute acid solution. The addition of acid ensured the pH of the sample was less than 5 at which point all bicarbonate is converted into $CO_2$.

Additionally, a desorption test of the enzyme was performed to evaluate the stability of CA attachment on the HFM. 10 mL of 50 mM phosphate buffer (pH 7.5) was circulated for 30 min in the shell compartment of the mini-lung module containing CA immobilized fibers, and then the solution was harvested for enzyme activity assay. We repeated the above procedures 3 times using the same module. The enzyme activities in the solutions were analyzed for the above samples.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A device for removal of at least a portion of carbon dioxide from an aqueous fluid, comprising: at least one structure through which carbon dioxide can pass to be removed from the fluid, the structure comprising a porous layer, a gas permeable, nonporous layer adjacent a surface of the porous layer, and immobilized carbonic anhydrase on a first surface of the nonporous layer to be contacted with the fluid such that the immobilized carbonic anhydrase comes into contact with the fluid, wherein the first surface exhibits carbonic anhydrase activity of at least 20% of maximum theoretical activity of the first surface of the nonporous layer based on monolayer surface coverage of carbonic anhydrase.

2. The device of claim 1 wherein the first surface exhibits carbonic anhydrase activity of at least 40% of maximum theoretical activity of the first surface of the membrane based on monolayer surface coverage of carbonic anhydrase.

3. The device of claim 1 wherein the first surface exhibits carbonic anhydrase activity of at least 60% of maximum theoretical activity of the first surface of the membrane based on monolayer surface coverage of carbonic anhydrase.

4. The device of claim 1 wherein the first surface exhibits carbonic anhydrase activity of at least 80% of maximum theoretical activity of the first surface of the membrane based on monolayer surface coverage of carbonic anhydrase.

5. The device of claim 3 wherein the fluid is blood and the nonporous layer is formed from a polymeric material.

6. The device of claim 5 wherein the carbonic anhydrase is immobilized on the polymeric material of the nonporous layer via adsorption, covalent bonding, ionic bonding or chelation.

7. The device of claim 5 wherein the carbonic anhydrase is covalently attached to the polymeric material of the nonporous layer.

8. The device of claim 7 wherein the material of the porous layer is microporous polymeric material through which carbon dioxide can pass.

9. The device of claim 8 wherein the polymeric material of the porous layer is microporous and hydrophobic.

10. The device of claim 9 wherein the polymeric material of the porous layer is an olefinic polymeric material.

11. The device of claim 8 wherein the carbonic anhydrase is covalently attached to the first surface of the nonporous layer and the porous layer is formed as a microporous polymeric hollow fiber.

12. The device of claim 11 wherein an interior lumen of the hollow fiber is adapted to have oxygen flow therethrough, the hollow fiber being adapted to pass oxygen into the blood while carbon dioxide passes from the blood to the interior lumen of the hollow fiber.

13. The device of claim 12 wherein the nonporous layer is formed from a siloxane nonporous polymer.

14. The device of claim 12 comprising a plurality of structures, wherein each of the plurality of structures comprises a porous layer, a gas permeable, nonporous layer adjacent a surface of the porous layer and immobilized carbonic anhydrase on a first surface of the nonporous layer, and wherein the porous layer of each structure is formed as a microporous polymeric hollow fiber.

15. The device of claim 1 wherein the nonporous layer comprises a carbon-dioxide-permeable siloxane polymer.

16. The device of claim 2 wherein the aqueous fluid comprise blood and the device further comprising free carbonic anhydrase to contact the blood.

17. The device of claim 1 wherein carbon dioxide is present in the fluid in the form of bicarbonate ion.

18. The device of claim 2 wherein the device is a component of a total liquid ventilation circuit adapted to be connected to lungs.

19. The device of claim 1 wherein the fluid is an oxygenated perfluorocarbon.

20. The device of claim 2 wherein the device uses peritoneal or gastric perfusion to provide respiratory support.

21. The device of claim 2 wherein the device is a component of an artificial lung.

22. The device of claim 7 wherein the polymeric material of the nonporous layer is treated prior to immobilizing the carbonic anhydrase thereon to create reactive sites on the polymeric material of the nonporous layer for covalent attachment of the carbonic anhydrase.

23. The device of claim 22 wherein the polymeric material of the nonporous layer is treated via radio frequency plasma discharge to create reactive sites upon the polymeric material.

24. The method of claim 23 wherein the reactive sites comprise at least one of a hydroxyl group, an amine group or a carboxyl group.

25. A method for removal of at least a portion of carbon dioxide from an aqueous fluid, comprising: placing at least one structure through which carbon dioxide can pass to be removed from the fluid in contact with the fluid, the structure comprising a porous layer, a gas permeable, nonporous layer adjacent a surface of the porous layer, and immobilized carbonic anhydrase on a first surface of the nonporous layer such that the immobilized carbonic anhydrase comes into contact with the fluid, wherein the first surface exhibits carbonic anhydrase activity of at least 20% of maximum theoretical activity of the first surface of the membrane based on monolayer surface coverage of carbonic anhydrase.

26. The method of claim 25 wherein the fluid is blood and the carbonic anhydrase is immobilized on the first surface of the nonporous layer.

27. The method of claim 26 wherein the first surface exhibits carbonic anhydrase activity of at least 40% of maximum theoretical activity of the first surface of the nonporous layer based on monolayer surface coverage of carbonic anhydrase.

28. The method of claim 26 wherein the first surface exhibits carbonic anhydrase activity of at least 60% of maximum theoretical activity of the first surface of the nonporous layer based on monolayer surface coverage of carbonic anhydrase.

29. The method of claim 26 wherein the first surface exhibits carbonic anhydrase activity of at least 80% of maximum theoretical activity of the first surface of the nonporous layer based on monolayer surface coverage of carbonic anhydrase.

30. The method of claim 28 wherein the nonporous layer is formed from a polymeric material.

31. The method of claim 30 wherein the carbonic anhydrase is immobilized on the polymeric material of the nonporous layer via adsorption, covalent bonding, ionic bonding or chelation.

32. The method of claim 31 wherein the carbonic anhydrase is covalently bonded to the polymeric material of the nonporous layer.

33. The method of claim 32 wherein carbonic anhydrase is contacted with the polymeric material of the nonporous layer to react with reactive groups on the polymeric material of the nonporous layer.

34. The method of claim 33 wherein the reactive groups on the polymeric material of the nonporous layer are reactive with amine groups on the carbonic anhydrase.

35. The method of claim 34 wherein the polymeric material of the nonporous layer is treated via radio frequency plasma discharge to create reactive sites upon the polymeric material of the nonporous layer for covalent attachment of the carbonic anhydrase.

36. The method of claim 35 wherein the reactive sites comprise at least one of a hydroxyl group, an amine group or a carboxyl group.

37. The method of claim 36 wherein the polymeric material of the nonporous layer is contacted with a cyanogen halide to react hydroxyl groups thereon with the cyanogen halide.

38. The method of claim 37 wherein carbonic anhydrase is contacted with the polymeric material of the nonporous layer after contacting cyanogen halide with the polymeric material.

39. The method of claim 38 wherein the cyanogen halide is cyanogen bromide.

40. The method of claim 35 wherein power levels during radio frequency plasma discharge and duration of radio frequency plasma discharge are maintained to prevent a significant increase in gas permeance of carbon dioxide-through the polymeric material of the nonporous layer.

41. The method of claim 40 wherein power levels during radio frequency plasma discharge and duration of radio frequency plasma discharge are maintained to prevent a significant increase in gas permeance of oxygen through the polymeric material of the nonporous layer.

42. The method of claim 32 wherein the porous layer comprises a microporous polymeric material.

43. The method of claim 42 wherein the aqueous fluid comprises blood and the porous layer is formed into a microporous hollow fiber having an interior lumen into which carbon dioxide can pass from the blood.

44. The method of claim 43 further comprising: causing oxygen to flow through the interior lumen of the microporous hollow fiber, whereby the oxygen can passes from the interior lumen into the blood.

45. A method of manufacturing a structure for use in removal of carbon dioxide from an aqueous fluid, the structure comprising a porous layer, a gas permeable and nonporous layer adjacent a surface of the porous layer, comprising:

immobilizing carbonic anhydrase on a first surface of a polymeric material of the nonporous layer via adsorption, covalent bonding, ionic bonding or chelation such that the first surface exhibits carbonic anhydrase activity of at least 20% of maximum theoretical activity of the first surface based on monolayer surface coverage of carbonic anhydrase.

46. The method of claim 45 wherein the carbonic anhydrase is covalently attached to the first surface of the polymeric material of the nonporous layer and the first surface of the polymeric material of the nonporous layer is treated prior to immobilizing the carbonic anhydrase thereon to create reactive sites on the polymeric material of the nonporous layer.

47. The method of claim 46 wherein the first surface of the polymeric material of the nonporous layer is treated via radio frequency plasma discharge to create reactive sites upon the first surface of the polymeric material of the nonporous layer.

48. The method of claim 47 wherein the reactive sites comprise at least one of a hydroxyl group, an amine group or a carboxyl group.

49. A device for removal of at least a portion of gaseous carbon dioxide from an aqueous fluid in which carbon dioxide can be reversibly converted to at least one other chemical entity, comprising: at least one structure through which gaseous carbon dioxide can pass to be removed from the fluid and at least one surface spaced from the structure, the spaced surface comprising carbonic anhydrase immobilized thereon, the spaced surface being positioned in the vicinity of a first surface of the structure, at least a portion of the carbonic anhydrase immobilized on the spaced surface being active to convert the at least one other chemical entity to gaseous carbon dioxide in the vicinity of the first surface of the structure.

50. The device of claim 49 wherein the spaced surface upon which carbonic anhydrase is immobilized comprises a polymeric material.

51. The device of claim 50 wherein the spaced surface upon which carbonic anhydrase is immobilized comprises a metal.

52. The device of claim 51 wherein the metal is gold.

53. The device of claim 52 wherein the gold is in the form of nanoparticles.

54. A device for removal of at least a portion of chemical entity from a fluid, comprising: at least one structure through which the chemical entity can pass as a gas to be removed from the fluid, the composite structure comprising a porous layer, a permeable, nonporous layer adjacent a surface of the porous layer, and immobilized enzyme on a first surface of the nonporous layer to be contacted with the fluid such that the immobilized enzyme comes into contact with the fluid, wherein the first surface exhibits enzyme activity of at least 20% of maximum theoretical activity of the first surface based on monolayer surface coverage of enzyme, and wherein the chemical entity is inter-convertible within the fluid to at least one other chemical entity that is not gaseous, the enzyme being adapted to catalyze a reaction of the other chemical entity to the chemical entity as a gas.

* * * * *